(12) United States Patent
Li et al.

(10) Patent No.: US 10,987,319 B2
(45) Date of Patent: Apr. 27, 2021

(54) TFEB ACTIVATOR C1 AMELIORATES APP AND TAU PATHOLOGY AND RESCUES COGNITIVE DEFICITS IN NEURODEGENERATIVE DISEASES

(71) Applicant: Hong Kong Baptist University, Hong Kong (HK)

(72) Inventors: Min Li, Hong Kong (HK); Juxian Song, Hong Kong (HK); Sandeep Malampati, Hong Kong (HK)

(73) Assignee: Hong Kong Baptist University, Hong Kong (HK)

( * ) Notice: Subject to any disclaimer, the term of this patent is extended or adjusted under 35 U.S.C. 154(b) by 0 days.

(21) Appl. No.: 16/455,787

(22) Filed: Jun. 28, 2019

(65) Prior Publication Data

US 2020/0000743 A1 Jan. 2, 2020

Related U.S. Application Data

(60) Provisional application No. 62/691,603, filed on Jun. 28, 2018.

(51) Int. Cl.
*A61K 31/12* (2006.01)
*A61P 25/28* (2006.01)

(52) U.S. Cl.
CPC .............. *A61K 31/12* (2013.01); *A61P 25/28* (2018.01)

(58) Field of Classification Search
None
See application file for complete search history.

(56) References Cited

U.S. PATENT DOCUMENTS

2015/0250741 A1* 9/2015 Li

OTHER PUBLICATIONS

Reagan-Shaw et. al., Dose translation from animal to human studies revisited, FASEB J. 2008;22(3):659-61.*
George S. Bloom, "Amyloid-β and Tau: The Trigger and Bullet in Alzheimer Disease Pathogenesis", JAMA Neurology, Apr. 2014, vol. 71, No. 4, p. 505-508.

* cited by examiner

*Primary Examiner* — Savitha M Rao
*Assistant Examiner* — Gregg Polansky
(74) *Attorney, Agent, or Firm* — Idea Intellectual Limited; Margaret A. Burke; Sam T. Yip

(57) ABSTRACT

The present invention relates to a method of use of a composition comprising an autophagy enhancement compound for treating neurodegenerative diseases. In particular, the said composition is used to treat the neural condition of synaptic dysfunction. Such neurodegenerative diseases include Parkinson's disease, Alzheimer's disease, Huntington's disease, Frontotemporal dementia with parkinsonism-17 (FTDP-17), Pick disease (PiD), Progressive supranuclear palsy (PSP), Corticobasal degeneration (CBD) and Cerebral amyloid angiopathy.

3 Claims, 10 Drawing Sheets
Specification includes a Sequence Listing.

SEQUENCE LISTING

```
<160> NUMBER OF SEQ ID NOS: 82

<210> SEQ ID NO 1
<211> LENGTH: 22
<212> TYPE: DNA
<213> ORGANISM: Artificial Sequence
<220> FEATURE:
<223> OTHER INFORMATION: ATG9B Forward Primer Human

<400> SEQUENCE: 1
accctgtcag atgccatcct ac                                               22

<210> SEQ ID NO 2
<211> LENGTH: 22
<212> TYPE: DNA
<213> ORGANISM: Artificial Sequence
<220> FEATURE:
<223> OTHER INFORMATION: ATG9B Reverse Primer Human

<400> SEQUENCE: 2
ccagtagctg aagaggttgc ag                                               22

<210> SEQ ID NO 3
<211> LENGTH: 23
<212> TYPE: DNA
<213> ORGANISM: Artificial Sequence
<220> FEATURE:
<223> OTHER INFORMATION: ATG10 Forward Primer Human

<400> SEQUENCE: 3
ggtgatagtt gggaatggag acc                                              23

<210> SEQ ID NO 4
<211> LENGTH: 22
<212> TYPE: DNA
<213> ORGANISM: Artificial Sequence
<220> FEATURE:
<223> OTHER INFORMATION: ATG10 Reverse Primer Human

<400> SEQUENCE: 4
gtctgtccat gggtagatgc tc                                               22

<210> SEQ ID NO 5
<211> LENGTH: 22
<212> TYPE: DNA
<213> ORGANISM: Artificial Sequence
<220> FEATURE:
<223> OTHER INFORMATION: ATG16L1 Forward Primer Human

<400> SEQUENCE: 5
ctacggaaga gaaccaggag ct                                               22
```

```
<210> SEQ ID NO 6
<211> LENGTH: 22
<212> TYPE: DNA
<213> ORGANISM: Artificial Sequence
<220> FEATURE:
<223> OTHER INFORMATION: ATG16L1 Reverse Primer Human

<400> SEQUENCE: 6
ctggtagagg ttcctttgct gc                                                  22

<210> SEQ ID NO 7
<211> LENGTH: 22
<212> TYPE: DNA
<213> ORGANISM: Artificial Sequence
<220> FEATURE:
<223> OTHER INFORMATION: BCL2 Forward Primer Human

<400> SEQUENCE: 7
atcgccctgt ggatgactga gt                                                  22

<210> SEQ ID NO 8
<211> LENGTH: 23
<212> TYPE: DNA
<213> ORGANISM: Artificial Sequence
<220> FEATURE:
<223> OTHER INFORMATION: BCL2 Reverse Primer Human

<400> SEQUENCE: 8
gccaggagaa atcaaacaga ggc                                                 23

<210> SEQ ID NO 9
<211> LENGTH: 22
<212> TYPE: DNA
<213> ORGANISM: Artificial Sequence
<220> FEATURE:
<223> OTHER INFORMATION: CLN3 Forward Primer Human

<400> SEQUENCE: 9
gaacacttcc ctgagtcacg ct                                                  22

<210> SEQ ID NO 10
<211> LENGTH: 22
<212> TYPE: DNA
<213> ORGANISM: Artificial Sequence
<220> FEATURE:
<223> OTHER INFORMATION: CLN3 Reverse Primer Human

<400> SEQUENCE: 10
aggtgaaacg gatgcgacag ca                                                  22

<210> SEQ ID NO 11
<211> LENGTH: 23
<212> TYPE: DNA
<213> ORGANISM: Artificial Sequence
<220> FEATURE:
<223> OTHER INFORMATION: GABARAPL1 Forward Primer Human

<400> SEQUENCE: 11
ttgtagagaa ggctccaaaa gcc                                                 23

<210> SEQ ID NO 12
<211> LENGTH: 22
<212> TYPE: DNA
<213> ORGANISM: Artificial Sequence
<220> FEATURE:
<223> OTHER INFORMATION: GABARAPL1 Reverse Primer Human
```

<400> SEQUENCE: 12
ggtctcaggt ggattctctt cc					22

<210> SEQ ID NO 13
<211> LENGTH: 22
<212> TYPE: DNA
<213> ORGANISM: Artificial Sequence
<220> FEATURE:
<223> OTHER INFORMATION: GABARAPL2 Forward Primer Human

<400> SEQUENCE: 13
ccagcttcct tctgaaaagg cg					22

<210> SEQ ID NO 14
<211> LENGTH: 22
<212> TYPE: DNA
<213> ORGANISM: Artificial Sequence
<220> FEATURE:
<223> OTHER INFORMATION: GABARAPL2 Reverse Primer Human

<400> SEQUENCE: 14
ttctctccgc tgtaggccac at					22

<210> SEQ ID NO 15
<211> LENGTH: 22
<212> TYPE: DNA
<213> ORGANISM: Artificial Sequence
<220> FEATURE:
<223> OTHER INFORMATION: MAP1LC3B Forward Primer Human

<400> SEQUENCE: 15
gagaagcagc ttcctgttct gg					22

<210> SEQ ID NO 16
<211> LENGTH: 22
<212> TYPE: DNA
<213> ORGANISM: Artificial Sequence
<220> FEATURE:
<223> OTHER INFORMATION: MAP1LC3B Reverse Primer Human

<400> SEQUENCE: 16
gtgtccgttc accaacagga ag					22

<210> SEQ ID NO 17
<211> LENGTH: 22
<212> TYPE: DNA
<213> ORGANISM: Artificial Sequence
<220> FEATURE:
<223> OTHER INFORMATION: MAPK14 Forward Primer Human

<400> SEQUENCE: 17
gagcgttacc agaacctgtc tc					22

<210> SEQ ID NO 18
<211> LENGTH: 23
<212> TYPE: DNA
<213> ORGANISM: Artificial Sequence
<220> FEATURE:
<223> OTHER INFORMATION: MAPK14 Reverse Primer Human

<400> SEQUENCE: 18
agtaaccgca gttctctgta ggt					23

<210> SEQ ID NO 19
<211> LENGTH: 22

```
<212> TYPE: DNA
<213> ORGANISM: Artificial Sequence
<220> FEATURE:
<223> OTHER INFORMATION: SQSTM1 Forward Primer Human

<400> SEQUENCE: 19
tgtgtagcgt ctgcgaggga aa                                              22

<210> SEQ ID NO 20
<211> LENGTH: 22
<212> TYPE: DNA
<213> ORGANISM: Artificial Sequence
<220> FEATURE:
<223> OTHER INFORMATION: SQSTM1 Reverse Primer Human

<400> SEQUENCE: 20
agtgtccgtg tttcaccttc cg                                              22

<210> SEQ ID NO 21
<211> LENGTH: 23
<212> TYPE: DNA
<213> ORGANISM: Artificial Sequence
<220> FEATURE:
<223> OTHER INFORMATION: VPS11 Forward Primer Human

<400> SEQUENCE: 21
gctataccaa gctcaaggac agc                                             23

<210> SEQ ID NO 22
<211> LENGTH: 22
<212> TYPE: DNA
<213> ORGANISM: Artificial Sequence
<220> FEATURE:
<223> OTHER INFORMATION: VPS11 Reverse Primer Human

<400> SEQUENCE: 22
atggttctcc gccagataca gg                                              22

<210> SEQ ID NO 23
<211> LENGTH: 22
<212> TYPE: DNA
<213> ORGANISM: Artificial Sequence
<220> FEATURE:
<223> OTHER INFORMATION: VPS18 Forward Primer Human

<400> SEQUENCE: 23
acttgggcaa ggcaaatgag cc                                              22

<210> SEQ ID NO 24
<211> LENGTH: 23
<212> TYPE: DNA
<213> ORGANISM: Artificial Sequence
<220> FEATURE:
<223> OTHER INFORMATION: VPS18 Reverse Primer Human

<400> SEQUENCE: 24
ccttctgtcc atttcggttc acg                                             23

<210> SEQ ID NO 25
<211> LENGTH: 22
<212> TYPE: DNA
<213> ORGANISM: Artificial Sequence
<220> FEATURE:
<223> OTHER INFORMATION: WIPI1 Forward Primer Human

<400> SEQUENCE: 25
```
cttcaagctg aacaggtca cc                                           22

<210> SEQ ID NO 26
<211> LENGTH: 22
<212> TYPE: DNA
<213> ORGANISM: Artificial Sequence
<220> FEATURE:
<223> OTHER INFORMATION: WIPI1 Reverse Primer Human

<400> SEQUENCE: 26
cggagaagtt caagcgtgca gt                                          22

<210> SEQ ID NO 27
<211> LENGTH: 22
<212> TYPE: DNA
<213> ORGANISM: Artificial Sequence
<220> FEATURE:
<223> OTHER INFORMATION: CLCN7 Forward Primer Human

<400> SEQUENCE: 27
cacagttgcc ttcgtgctga tc                                          22

<210> SEQ ID NO 28
<211> LENGTH: 22
<212> TYPE: DNA
<213> ORGANISM: Artificial Sequence
<220> FEATURE:
<223> OTHER INFORMATION: CLCN7 Reverse Primer Human

<400> SEQUENCE: 28
tggagttgta ctcgccatct gc                                          22

<210> SEQ ID NO 29
<211> LENGTH: 22
<212> TYPE: DNA
<213> ORGANISM: Artificial Sequence
<220> FEATURE:
<223> OTHER INFORMATION: ATP6V0E1 Forward Primer Human

<400> SEQUENCE: 29
ggtgacctgt tcagtttgct gc                                          22

<210> SEQ ID NO 30
<211> LENGTH: 23
<212> TYPE: DNA
<213> ORGANISM: Artificial Sequence
<220> FEATURE:
<223> OTHER INFORMATION: ATP6V0E1 Reverse Primer Human

<400> SEQUENCE: 30
gagcatgtct tcttcctcaa ggc                                         23

<210> SEQ ID NO 31
<211> LENGTH: 22
<212> TYPE: DNA
<213> ORGANISM: Artificial Sequence
<220> FEATURE:
<223> OTHER INFORMATION: ATP6V1H Forward Primer Human

<400> SEQUENCE: 31
cgggtcaatg agtaccgctt tg                                          22

<210> SEQ ID NO 32
<211> LENGTH: 23
<212> TYPE: DNA
<213> ORGANISM: Artificial Sequence

```
<220> FEATURE:
<223> OTHER INFORMATION: ATP6V1H Reverse Primer Human

<400> SEQUENCE: 32
gatactggag ctgaaagcca cac                                              23

<210> SEQ ID NO 33
<211> LENGTH: 22
<212> TYPE: DNA
<213> ORGANISM: Artificial Sequence
<220> FEATURE:
<223> OTHER INFORMATION: CTSA Forward Primer Human

<400> SEQUENCE: 33
gcttcgtgaa ggagttctcc ca                                               22

<210> SEQ ID NO 34
<211> LENGTH: 22
<212> TYPE: DNA
<213> ORGANISM: Artificial Sequence
<220> FEATURE:
<223> OTHER INFORMATION: CTSA Reverse Primer Human

<400> SEQUENCE: 34
ctgtggtcat cagtatggct gc                                               22

<210> SEQ ID NO 35
<211> LENGTH: 22
<212> TYPE: DNA
<213> ORGANISM: Artificial Sequence
<220> FEATURE:
<223> OTHER INFORMATION: CTSB Forward Primer Human

<400> SEQUENCE: 35
gcttcgatgc acgggaacaa tg                                               22

<210> SEQ ID NO 36
<211> LENGTH: 22
<212> TYPE: DNA
<213> ORGANISM: Artificial Sequence
<220> FEATURE:
<223> OTHER INFORMATION: CTSB Reverse Primer Human

<400> SEQUENCE: 36
cattggtgtg gatgcagatc cg                                               22

<210> SEQ ID NO 37
<211> LENGTH: 22
<212> TYPE: DNA
<213> ORGANISM: Artificial Sequence
<220> FEATURE:
<223> OTHER INFORMATION: CTSD Forward Primer Human

<400> SEQUENCE: 37
gcaaactgct ggacatcgct tg                                               22

<210> SEQ ID NO 38
<211> LENGTH: 23
<212> TYPE: DNA
<213> ORGANISM: Artificial Sequence
<220> FEATURE:
<223> OTHER INFORMATION: CTSD Reverse Primer Human

<400> SEQUENCE: 38
gccatagtgg atgtcaaacg agg                                              23
```

```
<210> SEQ ID NO 39
<211> LENGTH: 22
<212> TYPE: DNA
<213> ORGANISM: Artificial Sequence
<220> FEATURE:
<223> OTHER INFORMATION: CTSS Forward Primer Human

<400> SEQUENCE: 39
tggatcacca ctggcatctc tg                                              22

<210> SEQ ID NO 40
<211> LENGTH: 22
<212> TYPE: DNA
<213> ORGANISM: Artificial Sequence
<220> FEATURE:
<223> OTHER INFORMATION: CTSS Reverse Primer Human

<400> SEQUENCE: 40
gctccaggtt gtgaagcatc ac                                              22

<210> SEQ ID NO 41
<211> LENGTH: 22
<212> TYPE: DNA
<213> ORGANISM: Artificial Sequence
<220> FEATURE:
<223> OTHER INFORMATION: GALNS Forward Primer Human

<400> SEQUENCE: 41
agcagaccac gtttgaagga gg                                              22

<210> SEQ ID NO 42
<211> LENGTH: 22
<212> TYPE: DNA
<213> ORGANISM: Artificial Sequence
<220> FEATURE:
<223> OTHER INFORMATION: GALNS Reverse Primer Human

<400> SEQUENCE: 42
gtggtgaaga ggtccatgat gc                                              22

<210> SEQ ID NO 43
<211> LENGTH: 22
<212> TYPE: DNA
<213> ORGANISM: Artificial Sequence
<220> FEATURE:
<223> OTHER INFORMATION: GBA Forward Primer Human

<400> SEQUENCE: 43
tgctgctctc aacatccttg cc                                              22

<210> SEQ ID NO 44
<211> LENGTH: 22
<212> TYPE: DNA
<213> ORGANISM: Artificial Sequence
<220> FEATURE:
<223> OTHER INFORMATION: GBA Reverse Primer Human

<400> SEQUENCE: 44
taggtgcgga tggagaagtc ac                                              22

<210> SEQ ID NO 45
<211> LENGTH: 22
<212> TYPE: DNA
<213> ORGANISM: Artificial Sequence
<220> FEATURE:
<223> OTHER INFORMATION: GLA Forward Primer Human
```

```
<400> SEQUENCE: 45
gcaaccttga ctgccaggaa ga                                              22

<210> SEQ ID NO 46
<211> LENGTH: 23
<212> TYPE: DNA
<213> ORGANISM: Artificial Sequence
<220> FEATURE:
<223> OTHER INFORMATION: GLA Reverse Primer Human

<400> SEQUENCE: 46
ctcataacct gcatccttcc agc                                             23

<210> SEQ ID NO 47
<211> LENGTH: 22
<212> TYPE: DNA
<213> ORGANISM: Artificial Sequence
<220> FEATURE:
<223> OTHER INFORMATION: GNS Forward Primer Human

<400> SEQUENCE: 47
tccactgttg gttcgaggac ct                                              22

<210> SEQ ID NO 48
<211> LENGTH: 22
<212> TYPE: DNA
<213> ORGANISM: Artificial Sequence
<220> FEATURE:
<223> OTHER INFORMATION: GNS Reverse Primer Human

<400> SEQUENCE: 48
taggtcgtag ccagcaatgt cc                                              22

<210> SEQ ID NO 49
<211> LENGTH: 22
<212> TYPE: DNA
<213> ORGANISM: Artificial Sequence
<220> FEATURE:
<223> OTHER INFORMATION: HEXA Forward Primer Human

<400> SEQUENCE: 49
ggaggtcatt gaatacgcac gg                                              22

<210> SEQ ID NO 50
<211> LENGTH: 22
<212> TYPE: DNA
<213> ORGANISM: Artificial Sequence
<220> FEATURE:
<223> OTHER INFORMATION: HEXA Reverse Primer Human

<400> SEQUENCE: 50
ggattcactg gtccaaaggt gc                                              22

<210> SEQ ID NO 51
<211> LENGTH: 22
<212> TYPE: DNA
<213> ORGANISM: Artificial Sequence
<220> FEATURE:
<223> OTHER INFORMATION: LAMP1 Forward Primer Human

<400> SEQUENCE: 51
cgtgtcacga aggcgttttc ag                                              22

<210> SEQ ID NO 52
```

```
<211> LENGTH: 22
<212> TYPE: DNA
<213> ORGANISM: Artificial Sequence
<220> FEATURE:
<223> OTHER INFORMATION: LAMP1 Reverse Primer Human

<400> SEQUENCE: 52
ctgttctcgt ccagcagaca ct                                             22

<210> SEQ ID NO 53
<211> LENGTH: 22
<212> TYPE: DNA
<213> ORGANISM: Artificial Sequence
<220> FEATURE:
<223> OTHER INFORMATION: MCOLN1 Forward Primer Human

<400> SEQUENCE: 53
cggactgcta taccttcagc gt                                             22

<210> SEQ ID NO 54
<211> LENGTH: 22
<212> TYPE: DNA
<213> ORGANISM: Artificial Sequence
<220> FEATURE:
<223> OTHER INFORMATION: MCOLN1 Reverse Primer Human

<400> SEQUENCE: 54
ggtgcttaca ctcctggatg tg                                             22

<210> SEQ ID NO 55
<211> LENGTH: 22
<212> TYPE: DNA
<213> ORGANISM: Artificial Sequence
<220> FEATURE:
<223> OTHER INFORMATION: PSAP Forward Primer Human

<400> SEQUENCE: 55
gcctccaaga atgtcatccc tg                                             22

<210> SEQ ID NO 56
<211> LENGTH: 23
<212> TYPE: DNA
<213> ORGANISM: Artificial Sequence
<220> FEATURE:
<223> OTHER INFORMATION: PSAP Reverse Primer Human

<400> SEQUENCE: 56
caatcagctt ggtcacctcc ttc                                            23

<210> SEQ ID NO 57
<211> LENGTH: 22
<212> TYPE: DNA
<213> ORGANISM: Artificial Sequence
<220> FEATURE:
<223> OTHER INFORMATION: SCPEP1 Forward Primer Human

<400> SEQUENCE: 57
cattcagcga gggaccatca ag                                             22

<210> SEQ ID NO 58
<211> LENGTH: 22
<212> TYPE: DNA
<213> ORGANISM: Artificial Sequence
<220> FEATURE:
<223> OTHER INFORMATION: SCPEP1 Reverse Primer Human

<400> SEQUENCE: 58
```
cctctgccag acctttgtct tc                                        22

<210> SEQ ID NO 59
<211> LENGTH: 22
<212> TYPE: DNA
<213> ORGANISM: Artificial Sequence
<220> FEATURE:
<223> OTHER INFORMATION: SGSH Forward Primer Human

<400> SEQUENCE: 59
aatgccttca cctcggtcag ca                                        22

<210> SEQ ID NO 60
<211> LENGTH: 23
<212> TYPE: DNA
<213> ORGANISM: Artificial Sequence
<220> FEATURE:
<223> OTHER INFORMATION: SGSH Reverse Primer Human

<400> SEQUENCE: 60
tgtcgaagga gttgaagtgg tgc                                       23

<210> SEQ ID NO 61
<211> LENGTH: 22
<212> TYPE: DNA
<213> ORGANISM: Artificial Sequence
<220> FEATURE:
<223> OTHER INFORMATION: TFEB Forward Primer Human

<400> SEQUENCE: 61
cctggagatg accaacaagc ag                                        22

<210> SEQ ID NO 62
<211> LENGTH: 22
<212> TYPE: DNA
<213> ORGANISM: Artificial Sequence
<220> FEATURE:
<223> OTHER INFORMATION: TFEB Reverse Primer Human

<400> SEQUENCE: 62
taggcagctc ctgcttcacc ac                                        22

<210> SEQ ID NO 63
<211> LENGTH: 22
<212> TYPE: DNA
<213> ORGANISM: Artificial Sequence
<220> FEATURE:
<223> OTHER INFORMATION: TPP1 Forward Primer Human

<400> SEQUENCE: 63
ggtggcttca gcaatgtgtt cc                                        22

<210> SEQ ID NO 64
<211> LENGTH: 22
<212> TYPE: DNA
<213> ORGANISM: Artificial Sequence
<220> FEATURE:
<223> OTHER INFORMATION: TPP1 Reverse Primer Human

<400> SEQUENCE: 64
gaagtaactg gatggtggca gg                                        22

<210> SEQ ID NO 65
<211> LENGTH: 23
<212> TYPE: DNA

```
<213> ORGANISM: Artificial Sequence
<220> FEATURE:
<223> OTHER INFORMATION: TMEM55B Forward Primer Human

<400> SEQUENCE: 65
cagagttcac agaccgcact ttg                                          23

<210> SEQ ID NO 66
<211> LENGTH: 22
<212> TYPE: DNA
<213> ORGANISM: Artificial Sequence
<220> FEATURE:
<223> OTHER INFORMATION: TMEM55B Reverse Primer Human

<400> SEQUENCE: 66
ggcagtgact gccaaaagca ag                                           22

<210> SEQ ID NO 67
<211> LENGTH: 22
<212> TYPE: DNA
<213> ORGANISM: Artificial Sequence
<220> FEATURE:
<223> OTHER INFORMATION: GAPDH Forward Primer Human

<400> SEQUENCE: 67
gtctcctctg acttcaacag cg                                           22

<210> SEQ ID NO 68
<211> LENGTH: 22
<212> TYPE: DNA
<213> ORGANISM: Artificial Sequence
<220> FEATURE:
<223> OTHER INFORMATION: GAPDH Reverse Primer Human

<400> SEQUENCE: 68
accaccctgt tgctgtagcc aa                                           22

<210> SEQ ID NO 69
<211> LENGTH: 22
<212> TYPE: DNA
<213> ORGANISM: Artificial Sequence
<220> FEATURE:
<223> OTHER INFORMATION: Map1lc3a Forward Primer Rat

<400> SEQUENCE: 69
aacaggagaa ggatgaagac gg                                           22

<210> SEQ ID NO 70
<211> LENGTH: 22
<212> TYPE: DNA
<213> ORGANISM: Artificial Sequence
<220> FEATURE:
<223> OTHER INFORMATION: Map1lc3a Reverse Primer Rat

<400> SEQUENCE: 70
ttgactcaga agccgaaggt tt                                           22

<210> SEQ ID NO 71
<211> LENGTH: 22
<212> TYPE: DNA
<213> ORGANISM: Artificial Sequence
<220> FEATURE:
<223> OTHER INFORMATION: Lamp1 Forward Primer Rat

<400> SEQUENCE: 71
gcacctccaa ctattccctg aa                                           22
```

<210> SEQ ID NO 72
<211> LENGTH: 22
<212> TYPE: DNA
<213> ORGANISM: Artificial Sequence
<220> FEATURE:
<223> OTHER INFORMATION: Lamp1 Reverse Primer Rat

<400> SEQUENCE: 72
acagacccaa acctgtcact tt                                              22

<210> SEQ ID NO 73
<211> LENGTH: 22
<212> TYPE: DNA
<213> ORGANISM: Artificial Sequence
<220> FEATURE:
<223> OTHER INFORMATION: Tfeb Forward Primer Rat

<400> SEQUENCE: 73
aatgggagca accgtactta gg                                              22

<210> SEQ ID NO 74
<211> LENGTH: 22
<212> TYPE: DNA
<213> ORGANISM: Artificial Sequence
<220> FEATURE:
<223> OTHER INFORMATION: Tfeb Reverse Primer Rat

<400> SEQUENCE: 74
gagggaagac aggtccatga ag                                              22

<210> SEQ ID NO 75
<211> LENGTH: 22
<212> TYPE: DNA
<213> ORGANISM: Artificial Sequence
<220> FEATURE:
<223> OTHER INFORMATION: Atp6v1h Forward Primer Rat

<400> SEQUENCE: 75
ctcagtatgt gcagtgtgtt gc                                              22

<210> SEQ ID NO 76
<211> LENGTH: 22
<212> TYPE: DNA
<213> ORGANISM: Artificial Sequence
<220> FEATURE:
<223> OTHER INFORMATION: Atp6v1h Reverse Primer Rat

<400> SEQUENCE: 76
tacagttcac cccatctgct tc                                              22

<210> SEQ ID NO 77
<211> LENGTH: 22
<212> TYPE: DNA
<213> ORGANISM: Artificial Sequence
<220> FEATURE:
<223> OTHER INFORMATION: Vps18 Forward Primer Rat

<400> SEQUENCE: 77
gctgatgatt cgctccattg ac                                              22

<210> SEQ ID NO 78
<211> LENGTH: 22
<212> TYPE: DNA
<213> ORGANISM: Artificial Sequence
<220> FEATURE:

```
<223> OTHER INFORMATION: Vps18 Reverse Primer Rat

<400> SEQUENCE: 78
agtctggtag ctgtatccct gt                                              22

<210> SEQ ID NO 79
<211> LENGTH: 22
<212> TYPE: DNA
<213> ORGANISM: Artificial Sequence
<220> FEATURE:
<223> OTHER INFORMATION: Actb Forward Primer Rat

<400> SEQUENCE: 79
ctgtgtggat tggtggctct at                                              22

<210> SEQ ID NO 80
<211> LENGTH: 22
<212> TYPE: DNA
<213> ORGANISM: Artificial Sequence
<220> FEATURE:
<223> OTHER INFORMATION: Actb Reverse Primer Rat

<400> SEQUENCE: 80
gtaacagtcc gcctagaagc at                                              22

<210> SEQ ID NO 81
<211> LENGTH: 20
<212> TYPE: DNA
<213> ORGANISM: Artificial Sequence
<220> FEATURE:
<223> OTHER INFORMATION: APP forward primer

<400> SEQUENCE: 81
aggactgacc actcgaccag                                                 20

<210> SEQ ID NO 82
<211> LENGTH: 19
<212> TYPE: DNA
<213> ORGANISM: Artificial Sequence
<220> FEATURE:
<223> OTHER INFORMATION: APP reverse primer

<400> SEQUENCE: 82
cgggggtcta gttctgcat                                                  19
```

TFEB ACTIVATOR C1 AMELIORATES APP AND TAU PATHOLOGY AND RESCUES COGNITIVE DEFICITS IN NEURODEGENERATIVE DISEASES

CROSS-REFERENCE TO RELATED APPLICATIONS

This application claims the benefit of U.S. Provisional Patent Application Ser. No. 62/691,603 filed on Jun. 28, 2018, the disclosure of which is hereby incorporated by reference.

FIELD OF INVENTION

The present invention relates to a composition comprising an autophagy enhancement compound which is blood-brain barrier permeable, MTOR-independent, and transcription factor EB (TFEB) gene-activating. In particular, the present invention relates to a composition comprising a small molecule being able to enhance autophagy and lysosome biogenesis by activating the gene TFEB which can clear toxic protein aggregates, restore synaptic plasticity and improve cognitive function for treating neurodegenerative diseases such as Parkinson's disease, Alzheimer's disease, Huntington's disease, Frontotemporal dementia with parkinsonism-17 (FTDP-17), Pick disease (PiD), Progressive supranuclear palsy (PSP), Corticobasal degeneration (CBD) and Cerebral amyloid angiopathy.

BACKGROUND OF INVENTION

Macroautophagy, herein referred to as autophagy, is a highly conserved process for cellular degradation and recycling of cytosolic contents to maintain cellular homeostasis. Autophagy substrates are generally cellular organelles, long-lived proteins and aggregate-prone proteins. Due to its functionality to clear cytosolic contents, this highly conserved process has been shown to be a promising approach for treatment of diseases characterized by the formation of intracellular aggregates, such as aging of the brain and neurodegeneration.

Dysfunction in the autophagy-lysosome pathway (ALP) has been directly linked to neurodegenerative disorders. Recently, the transcription factor EB (TFEB) has been identified in Settembre, C., et. al., *TFEB links autophagy to lysosomal biogenesis*. Science, 2011. 332(6036): 1429-33, and Sardiello, M., et al., *A gene network regulating lysosomal biogenesis and function*. Science, 2009. 325(5939): 473-7, as a master regulator of ALP. TFEB transgene to increase TFEB expression, or small molecules aimed to stimulate nuclear translocation of endogenous TFEB promotes the clearance of toxic protein aggregates, thus providing a disease-modifying intervention for neurodegenerative disorders such as Parkinson's disease (PD), Alzheimer's disease (AD) and Huntington's disease (HD).

Current MTOR inhibitors, such as rapamycin and torin 1, activate TFEB by promoting TFEB nuclear translocation. However, their pharmacokinetic profile and side effects make them less likely to be useful for long-term use in patients with neurodegenerative diseases. Disaccharides, such as trehalose and sucrose, activate TFEB in an MTOR-independent manner and may be beneficial for neurodegenerative diseases. However, the blood-brain barrier (BBB) permeability of trehalose and sucrose is poor. Discovery of small molecules which directly target TFEB hold great promise for the development of efficient neuroprotective therapies.

SUMMARY OF THE INVENTION

Accordingly, it is an objective of the present invention to provide a small molecule compound having good BBB permeability and potent TFEB-activating effects for the treatment of neurodegenerative diseases. The present invention provides a compound having simple chemical structure which can be easily synthesized in large scale. The present invention provides a compound that directly binds to and activates TFEB without inhibiting MTOR pathway, thus eliminating possible MTOR-associated complications, and while ameliorates APP and Tau pathologies to improve cognitive deficits in neurodegenerative diseases such as Alzheimer's disease. A further objective of the present invention is to provide a method for reversing synaptic dysfunction, ameliorating memory deficits and/or reducing beta-amyloid and aggregated Tau proteins in a subject in need thereof, thereby treating lysosomal storage disorders and diseases that can benefit from autophagy, including but not limited to neurodegenerative disorders, immunological diseases, cardiac diseases and cancer.

The present invention relates to a composition comprising an autophagy enhancement compound which is blood-brain barrier permeable, MTOR-independent, and TFEB gene-activating. In particular, the present invention relates to a composition comprising a small molecule being able to enhance autophagy and lysosome biogenesis by activating the gene TFEB which can clear toxic protein aggregates, restore synaptic plasticity and improve cognitive function in order for treating neurodegenerative diseases such as Parkinson's disease, Alzheimer's disease, Huntington's disease, Frontotemporal dementia with parkinsonism-17 (FTDP-17), Pick disease (PiD), Progressive supranuclear palsy (PSP), Corticobasal degeneration (CBD) and Cerebral amyloid angiopathy.

The present invention discloses a potent activator of TFEB that enhances autophagy and lysosome biogenesis in neuronal and non-neuronal cells. In comparison to currently known TFEB activators, the advantages of the present invention are: 1) The compound of the present invention is a small lipid molecule with good BBB permeability and potent TFEB-activating property; 2) The chemical structure of the compound of the present invention is simple and it can be easily synthesized in large scale for pre-clinical and clinical studies; 3) Compound of the present invention activates TFEB without inhibiting MTOR pathway, thus eliminating possible MTOR-associated complications in clinical trials. Therefore, the present invention has a wide field of application in the treatment of lysosomal storage disorders and common neurodegenerative diseases.

In a first aspect of the present invention, there is provided a composition comprising an effective amount of an autophagy enhancer with a formula of C1:

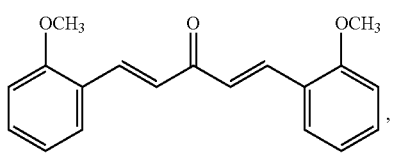

which induces autophagy in neuronal and non-neuronal cells, more specifically, in neuronal or neuronal-like cells. The compound is a synthesized mono-carbonyl analog of curcumin and its chemical name is 1,5-bis(2-methoxyphenyl)penta-1,4-dien-3-one.

In another embodiment of the present invention, it is provided that the compound of C1 promotes the degradation of wild-type and A53T mutant alpha-synuclein (SNCA) in cell culture.

In yet a further embodiment of the present invention, there is provided that compound of C1 activates transcription factor EB (TFEB), an essential regulator of autophagy and lysosome biogenesis. C1 significantly increases endogenous TFEB expression and promotes the nuclear translocation of TFEB.

It is known that MTOR pathway is a key regulator of cell growth and proliferation. In another embodiment of the present invention there is provided that compound C1 activates TFEB-mediated autophagy without inhibiting MTOR pathway.

In yet a further embodiment of the present invention, there is provided that C1 directly binds to TFEB and inhibits MTOR-TFEB-YWHA interaction, which releases TFEB from MTOR complex and promotes TFEB nuclear translocation.

In yet another embodiment of the present invention, there is provided that compound C1 enhances TFEB-mediated autophagy and lysosome biogenesis in non-neuronal cells and neuronal cells.

In yet another embodiment of the present invention there is provided that short-term oral administration of curcumin analog C1 activates TFEB and autophagy, and chronic administration of C1 promotes the degradation of endogenous SNCA.

A second aspect of the present invention provides a method for treating neurodegenerative disorders caused by or associated with synaptic dysfunction, memory deficits and/or high level of beta-amyloid and aggregated Tau proteins in a subject's brain, but without obvious side effects caused by mTOR inhibition, said method comprising administering a composition comprising an effective amount of compound of formula C1 to said subject in need of the composition. Such neurodegenerative diseases comprise but are not limited to the following: Alzheimer's disease, Parkinson's disease, Huntington's disease, Creutzfeldt-Jakob disease Frontotemporal dementia with parkinsonism-17, Pick disease, Progressive supranuclear palsy, Corticobasal degeneration and Cerebral amyloid angiopathy.

In an embodiment of the second aspect of the present invention, compound of formula C1 is administered at 0.41 mg/kg to 28.38 mg/kg per body weight of the subject in need thereof, and the subject is adult human. Preferably, the compound of formula C1 is administered to the subject at less than 1.62 mg/kg per body weight of said subject daily. More preferably, the compound of formula C1 is administered to said subject from 0.41 to less than 1.62 mg/kg per body weight of the subject daily.

In another embodiment of the second aspect of the present invention, the composition is administered via oral administration and/or intravenous injection. More preferably, the composition is administered orally.

In yet another embodiment, the composition is orally administered once a day or daily (q.d.) for at least three consecutive months to said subject in need thereof.

In another embodiment of the second aspect of the present invention, wherein levels of beta-amyloid plaque load, carboxy terminal fragments of amyloid precursor protein and phosphorylated Tau in cortico-hippocampal section of the brain of said subject are reduced after said administering.

A third aspect of the present invention provides a method for enhancing autophagy in cells comprising providing a mono-carbonyl analog of curcumin having a formula of

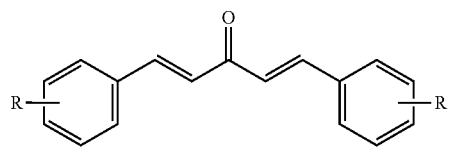

wherein R is selected from $OCH_3$.

In an exemplary embodiment of the third aspect of the present invention, the mono-carbonyl analog of curcumin having the formula of C1:

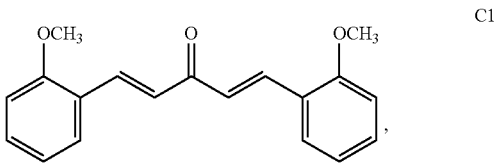 [SMILES: COc1ccccc1/C=C/C(=O)/C=C/c1ccccc1OC]

1,5-bis(2-methoxyphenyl)penta-1,4-dien-3-one.

In a fourth aspect of the present invention, there is provided a method for enhancing lysosome biogenesis in cells comprising providing a mono-carbonyl analogs of curcumin having a formula of

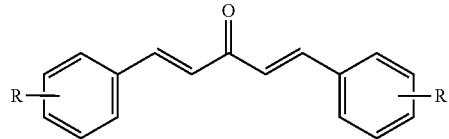

wherein R is OCH3.

In a first embodiment of the fourth aspect of the present invention the mono-carbonyl analog of curcumin having a formula of C1:

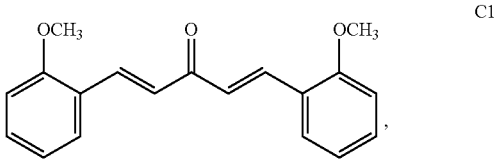 [SMILES: COc1ccccc1/C=C/C(=O)/C=C/c1ccccc1OC]

1,5-bis(2-methoxyphenyl)penta-1,4-dien-3-one.

In a second embodiment of the fourth aspect of the present invention, the mono-carbonyl analog binds to and activates TFEB in cells.

In the third and fourth aspects of the present invention, the cells are non-neuronal cells or neuronal cells.

In a fifth aspect of the present invention there is presented a method of promoting the degradation of Tau aggregates in biological cells of a subject in need thereof comprising administering a composition comprising a mono-carbonyl analog of curcumin having a formula of C1:

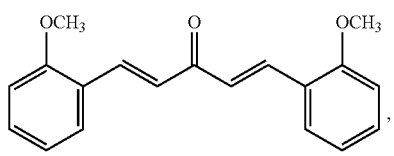

1,5-bis(2-methoxyphenyl)penta-1,4-dien-3-one.

In a first embodiment of the fifth aspect of the present invention wherein said mono-carbonyl analog of curcumin is administered to the subject in need thereof via oral administration.

In a second embodiment of the fifth aspect of the present invention wherein said biological cells are neuronal cells.

Throughout the present specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the present invention.

Furthermore, throughout the present specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the present invention and apply throughout. Unless otherwise defined, all other technical terms used herein have the same meaning as commonly understood to one of ordinary skill in the art to which the invention belongs.

Other aspects and advantages of the present invention will be apparent to those skilled in the art from a review of the ensuing description.

BRIEF DESCRIPTION OF THE DRAWINGS

The patent or patent application file contains at least one drawing executed in color. Copies of this patent or patent application publication with color drawing(s) will be provided by the Office upon request and payment of the necessary fee.

The above and other objects and features of the present invention will become apparent from the following description of the invention, when taken in conjunction with the accompanying drawings, in which:

FIG. 9A shows representative current and mean slope fEPSP percentage of WT, 5×FAD-Veh and 5×FAD-C1 groups after TBS stimulation, recorded using MED64 multielectrode array system; FIG. 9B shows mean fEPSP slope percentage increase from baseline was significantly increased in WT and 5×FAD-C1 group compared to 5×FAD-Veh group. (n=8 recordings of 6 mice from each group, ***P<0.001).

DETAILED DESCRIPTION OF THE INVENTION

Figure 1:
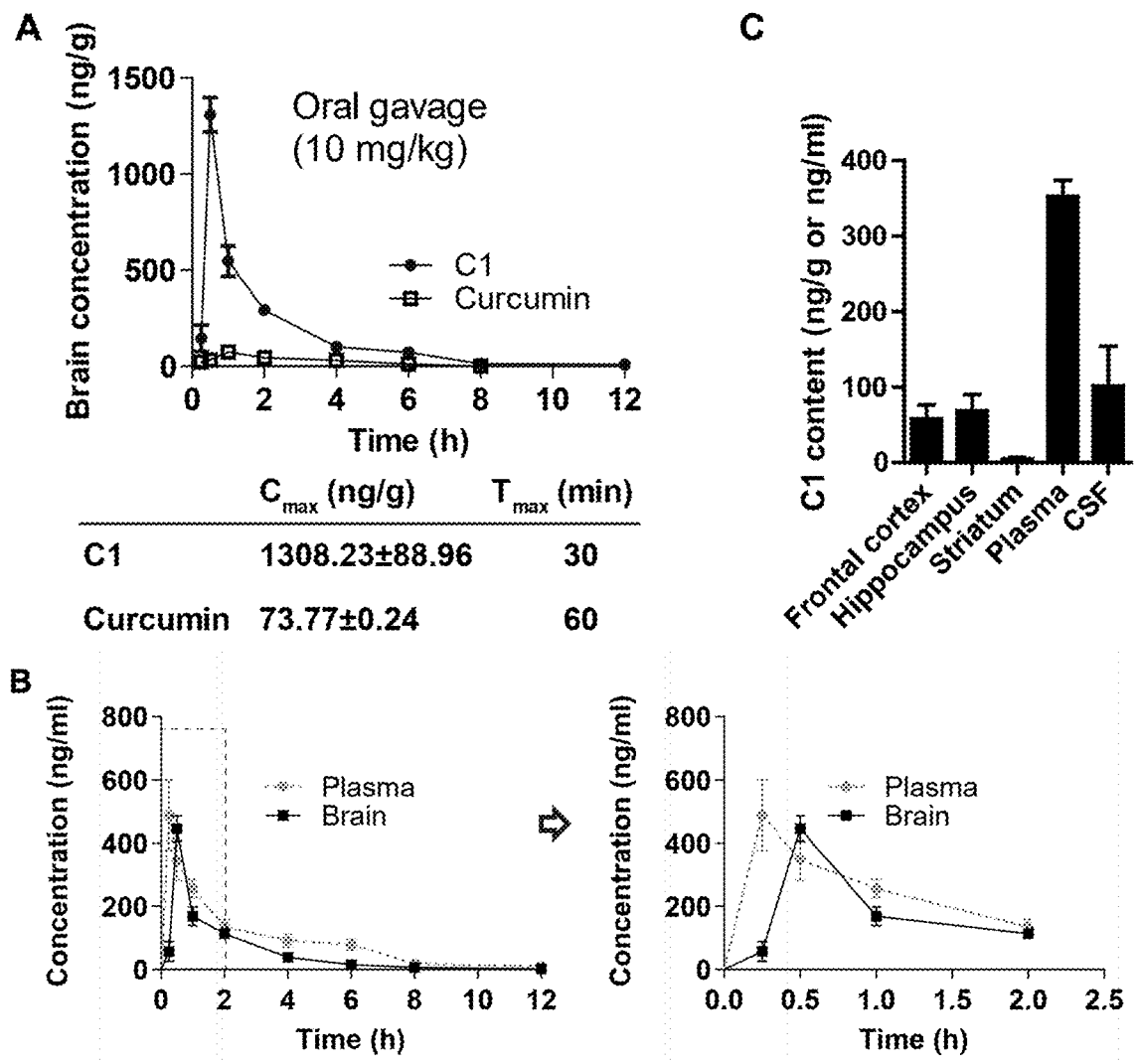
FIG. 1 shows pharmacokinetic profiles of curcumin analog C1 and curcumin: (A) Time-course curve of C1 and curcumin concentration (ng/g) in the brains of mice orally treated with indicated compounds (10 mg/kg). Values are expressed as Mean±SEM (n=3); (B) Parallel time-course curve of C1 distribution in the brain and blood respectively. Values are expressed as Mean±SEM (n=3); (C) Mice were orally treated with C1 (10 mg/kg) and the content of C1 in frontal cortex, hippocampus and striatum of the brain (weighted as ng/g), plasma and CSF (weighted as ng/ml) was quantified 30 min after drug administration. Values are expressed as Mean±SEM (n=4).

The present invention is not to be limited in scope by any of the specific embodiments described herein. The following embodiments are presented for exemplification only.

Definitions

"a," "an," and "the" as used herein include "at least one" and "one or more" unless stated otherwise. Thus, for example, reference to "a pharmacologically acceptable carrier" includes mixtures of two or more carriers as well as a single carrier, and the like.

The term "autophagy" refers to macroautophagy, unless stated otherwise, is the catabolic process involving the degradation of a cell's own components; such as, long lived proteins, protein aggregates, cellular organelles, cell membranes, organelle membranes, and other cellular components. The mechanism of autophagy may include: (i) the formation of a membrane around a targeted region of the cell, separating the contents from the rest of the cytoplasm, (ii) the fusion of the resultant vesicle with a lysosome and the subsequent degradation of the vesicle contents. The term autophagy may also refer to one of the mechanisms by which a starving cell re-allocates nutrients from unnecessary processes to more essential processes. Also, for example, autophagy may inhibit the progression of some diseases and play a protective role against infection by intracellular pathogens.

The diseases that benefit from autophagy inducement are diseases of which conditions are ameliorated, reduced or eliminated by autophagy and can be treated by the inventions as disclosed herein. The diseases include aggregate-prone disorder which represents any disease, disorder or condition associated with or caused by abnormal protein aggregates that are not sufficiently destroyed by a natural autophagy process in an organism and can be treated through degradation thereof via induction of autophagy by the subject invention. For example, such diseases include Alzheimer's disease, Parkinson's disease, amyotrophic lateral sclerosis, Huntington's disease, spinocerebellar ataxia, oculopharyngeal muscular dystrophy, prion diseases, fatal familial insomnia, alpha-1 antitrypsin deficiency, dentatorubral pallidoluysian atrophy, frontal temporal dementia, progressive supranuclear palsy, x-linked spinobulbar muscular atrophy, and neuronal intranuclear hyaline inclusion disease. The diseases also include cancer e.g., any cancer wherein the induction of autophagy would inhibit cell growth and division, reduce mutagenesis, remove mitochondria and other organelles damaged by reactive oxygen species or kill developing tumor cells. They can be chronic diseases which refers to persistent and lasting diseases, medical conditions or diseases that have developed slowly. The diseases that can be treated by the subject invention also include, but not limited to, cardiovascular disorders, autoimmune disorders, metabolic disorders, hamartoma syndrome, genetic muscle disorders, and myopathies.

The present invention provides a small molecule being able to enhance autophagy and lysosome biogenesis by activating TFEB. The molecule is a mono-carbonyl analog of curcumin. The molecule directly binds to TFEB, promote its expression and nuclear translocation. The molecule can prevent the accumulation of toxic protein aggregates in treating neurodegenerative diseases such as Parkinson's, Alzheimer's and Huntington's diseases. The molecule activates TFEB without inhibiting MTOR pathway, which is a key regulator of cell growth and proliferation.

TFEB has been identified as a master gene regulating lysosome biogenesis and autophagy. Pharmacological activation of TFEB promotes cellular clearance of accumulated toxic molecules. The present invention discloses a potent activator of TFEB that enhances autophagy and lysosome biogenesis in neuronal and non-neuronal cells. In comparison to currently known TFEB activators, the advantages of the present invention are: 1) compound of the present invention is a small lipid molecule with good BBB permeability and potent TFEB-activating effects for treating neurodegenerative diseases; 2) chemical structure of compound of the present invention is simple and it can be easily synthesized in large scale for pre-clinical and clinical studies; 3) compound of the present invention activates TFEB without inhibiting MTOR pathway, thus eliminating possible MTOR-associated complications in clinical trials. Therefore, the present invention has a wide field of application in the treatment of lysosomal storage disorders and common neurodegenerative diseases.

The present invention provides a method for enhancing autophagy in cells comprising providing a mono-carbonyl analog of curcumin having a formula of

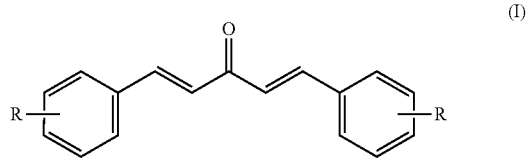

(I)

wherein R is selected from OCH$_3$.

In an exemplary embodiment of the present invention, the mono-carbonyl analog of curcumin having a formula of C1:

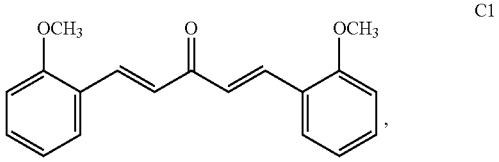 [SMILES: COc1ccccc1/C=C/C(=O)/C=C/c1ccccc1OC]

C1

1,5-bis(2-methoxyphenyl)penta-1,4-dien-3-one.

In a second aspect of the present invention there is provided a method for enhancing lysosome biogenesis in cells comprising providing a mono-carbonyl analog of curcumin having a formula of

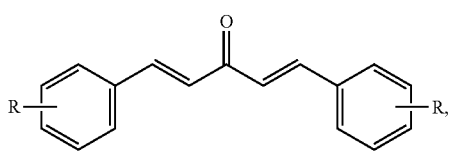

(I)

wherein R is OCH3.

In a first embodiment of the second aspect of the present invention there is provided a method for enhancing lysosome biogenesis in cells comprising providing a mono-carbonyl analog of curcumin having a formula of C1:

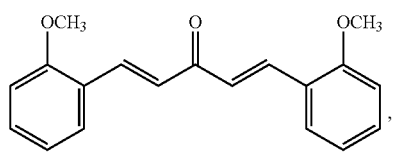

C1

1,5-bis(2-methoxyphenyl)penta-1,4-dien-3-one.

In a second embodiment of the second aspect of the present invention, the mono-carbonyl analog binds to and activates TFEB in cells.

In yet another embodiment of the present invention, the cells are non-neuronal cells or neuronal cells.

In a third aspect of the present invention there is provided a method of treating neurodegenerative diseases comprising administering a composition comprising a mono-carbonyl analog of Formula (I) to a subject in need thereof, wherein R is selected from $OCH_3$.

In a first embodiment of the third aspect of the present invention, the neurodegenerative diseases comprising Alzheimer's disease, Parkinson's disease, Huntington's disease and Creutzfeldt-Jakob disease.

In a second embodiment of the third aspect of the present invention, the composition comprises 0.41 mg/kg to 28.38 mg/kg of C1. More specifically, the composition comprises from 0.41 to less than 1.62 mg/kg of C1 per body weight of the subject being administered with the composition.

In a third embodiment of the third aspect of the present invention, the composition is administered via oral administration, intravenous injection or both.

The embodiments of the present invention are further illustrated by the following working examples, which should not be construed as further limiting.

EXAMPLES

In the following examples, the following materials are used; various commercial sources for the materials are provided. Details of the various protocols are also set forth below:

Reagents and Antibodies.

The trial samples of mono-carbonyl analogs of curcumin are kindly provided by Dr. Zhou Bo (Lanzhou University, China). Compound C1 ((1E,4E)-1,5-bis(2-methoxy-phenyl) penta-1,4-dien-3-one) is synthesized from 2-methoxybenz- aldehyde in an one-step reaction. The structure and purity of the compound are confirmed by 1H NMR and HPLC. Curcumin (08511), chloroquine (C6628), doxycycline (D9891), Anti-Flag M2 (F1804) are purchased from Sigma-Aldrich. Torin 1 (2273-5) is purchased from BioVision Inc. Anti-phospho-AKT (ser473) (9271), anti-AKT (9272), anti-phospho-MTOR (Ser2448) (2971), anti-MTOR (2983), anti-phospho-P70S6K/RPS6KB1 (Thr389) (9234) and anti-P70S6K/RPS6KB1 (9202), pan-14-3-3/YWHA (8312) antibodies are purchased from Cell Signaling Technology. Anti-á-syn/SNCA antibody (610786) is purchased from BD Transduction Laboratories. HRP-conjugated goat anti-mouse (115-035-003) and goat anti-rabbit (111-035-003) secondary antibodies are purchased from Jackson ImmunoResearch. Anti-â-actin/ACTB (sc-47778) is purchased from Santa Cruz Biotechnology. Anti-ATG5 (NB110-53818) and anti-LC3 (NB100-2220) antibodies were purchased from Novus Biologicals. Anti-TFEB (13372-1-AP) was purchased from Proteintech. Mouse Atg5 siRNA (L-064838-00-0005) and non-target siRNA, human TFEB siRNA (M-009798-02-0005) and non-target siRNA are purchased from Dharmacon. DMEM (11965-126), FBS (10270-106), Opti-MEM I (31985-070), horse serum (16050-122), Hygromycin B (10687-010), G418 (10131-035), Alexa Fluor®488 goat anti-mouse IgG (A-11001) and Alexa Fluor®594 goat anti-rabbit IgG (A-11012) are purchased from Life Technologies.

Cell Culture and Drug Treatment.

N2a, Hela and Hela cells stably expressing 3×-Flag-TFEB are cultured in DMEM supplemented with 10% FBS. SH-SY5Y cells are cultured in DMEM/F12 supplemented with 10% FBS. For drug treatment, the full medium is replaced by fresh Opti-MEM I and then the compounds (in 0.1% DMSO) are added to the cells and incubated for 12 h. Inducible PC12 cells overexpressing SNCA (WT and A53T) (a kind gift from Prof. David C. Rubinsztein at Cambridge University) are grown in DMEM supplemented with 10% horse serum, 5% FBS, 50 µg/ml G418, and 150 µg/ml hygromycin B at 37° C., 10% CO2. Cells are treated with 2 µg/ml doxycycline (Dox) for 24 h to induce SNCA expression. The full medium is changed to Opti-MEM I containing the testing compounds for another 48 h.

LDH Assay.

The cytotoxicity is determined by measurement of LDH release from damaged cells using LDH Kit (11644793001, Roche) according to the manufacturer's protocol.

siRNA Knock-Down.

Mouse Atg5 siRNA (25 nM) or human TFEB (100 nM) siRNA and the non-target siRNAs are transfected with Lipofectamine RNAiMAX (Ser. No. 13/778,030, Invitrogen) and incubated at 37° C. for 72 h.

Quantitative Real-Time PCR.

Total RNA is extracted from cells and tissues using RNeasy Plus Mini Kit (74134, Qiagen). Reverse transcription is performed using High-Capacity cDNA Reverse Transcription Kit (4368814, Life Technologies). Autophagy and lysosome gene primers are synthesized by Life Technologies and the oligonucleotide sequences are listed in Table 1. Real-time PCR is carried out with the Fast SYBRR Green Master Mix (4385612, Life Technologies) using the ViiA™ 7 Real-Time PCR System (Life Technologies). Fold changes are calculated using the ΔΔCT method and the results were normalized against an internal control (GAPDH or ACTB).

TABLE 1

Primer sequences used in real-time PCR analysis.

| SEQ ID No. | Gene name | Forward primer | SEQ ID No. | Reverse primer |
|---|---|---|---|---|
| | Human primers | | | |
| 1 | ATG9B | ACCCTGTCAGATGCCATCCTAC | 2 | CCAGTAGCTGAAGAGGTTGCAG |
| 3 | ATG10 | GGTGATAGTTGGGAATGGAGACC | 4 | GTCTGTCCATGGGTAGATGCTC |
| 5 | ATG16L1 | CTACGGAAGAGAACCAGGAGCT | 6 | CTGGTAGAGGTTCCTTTGCTGC |
| 7 | BCL2 | ATCGCCCTGTGGATGACTGAGT | 8 | GCCAGGAGAAATCAAACAGAGGC |
| 9 | CLN3 | GAACACTTCCCTGAGTCACGCT | 10 | AGGTGAAACGGATGCGACAGCA |
| 11 | GABARAPL1 | TTGTAGAGAAGGCTCCAAAAGCC | 12 | GGTCTCAGGTGGATTCTCTTCC |
| 13 | GABARAPL2 | CCAGCTTCCTTCTGAAAAGGCG | 14 | TTCTCTCCGCTGTAGGCCACAT |
| 15 | MAP1LC3B | GAGAAGCAGCTTCCTGTTCTGG | 16 | GTGTCCGTTCACCAACAGGAAG |
| 17 | MAPK14 | GAGCGTTACCAGAACCTGTCTC | 18 | AGTAACCGCAGTTCTCTGTAGGT |
| 19 | SQSTM1 | TGTGTAGCGTCTGCGAGGGAAA | 20 | AGTGTCCGTGTTTCACCTTCCG |
| 21 | VPS11 | GCTATACCAAGCTCAAGGACAGC | 22 | ATGGTTCTCCGCCAGATACAGG |
| 23 | VPS18 | ACTTGGGCAAGGCAAATGAGCC | 24 | CCTTCTGTCCATTTCGGTTCACG |
| 25 | WIPI1 | CTTCAAGCTGGAACAGGTCACC | 26 | CGGAGAAGTTCAAGCGTGCAGT |
| 27 | CLCN7 | CACAGTTGCCTTCGTGCTGATC | 28 | TGGAGTTGTACTCGCCATCTGC |
| 29 | ATP6V0E1 | GGTGACCTGTTCAGTTTGCTGC | 30 | GAGCATGTCTTCTTCCTCAAGGC |
| 31 | ATP6V1H | CGGGTCAATGAGTACCGCTTTG | 32 | GATACTGGAGCTGAAAGCCACAC |
| 33 | CTSA | GCTTCGTGAAGGAGTTCTCCCA | 34 | CTGTGGTCATCAGTATGGCTGC |
| 35 | CTSB | GCTTCGATGCACGGGAACAATG | 36 | CATTGGTGTGGATGCAGATCCG |
| 37 | CTSD | GCAAACTGCTGGACATCGCTTG | 38 | GCCATAGTGGATGTCAAACGAGG |
| 39 | CTSS | TGGATCACCACTGGCATCTCTG | 40 | GCTCCAGGTTGTGAAGCATCAC |
| 41 | GALNS | AGCAGACCACGTTTGAAGGAGG | 42 | GTGGTGAAGAGGTCCATGATGC |
| 43 | GBA | TGCTGCTCTCAACATCCTTGCC | 44 | TAGGTGCGGATGGAGAAGTCAC |
| 45 | GLA | GCAACCTTGACTGCCAGGAAGA | 46 | CTCATAACCTGCATCCTTCCAGC |
| 47 | GNS | TCCACTGTTGGTTCGAGGACCT | 48 | TAGGTCGTAGCCAGCAATGTCC |
| 49 | HEXA | GGAGGTCATTGAATACGCACGG | 50 | GGATTCACTGGTCCAAAGGTGC |
| 51 | LAMP1 | CGTGTCACGAAGGCGTTTTCAG | 52 | CTGTTCTCGTCCAGCAGACACT |
| 53 | MCOLN1 | CGGACTGCTATACCTTCAGCGT | 54 | GGTGCTTACACTCCTGGATGTG |
| 55 | PSAP | GCCTCCAAGAATGTCATCCCTG | 56 | CAATCAGCTTGGTCACCTCCTTC |
| 57 | SCPEP1 | CATTCAGCGAGGGACCATCAAG | 58 | CCTCTGCCAGACCTTTGTCTTC |
| 59 | SGSH | AATGCCTTCACCTCGGTCAGCA | 60 | TGTCGAAGGAGTTGAAGTGGTGC |
| 61 | TFEB | CCTGGAGATGACCAACAAGCAG | 62 | TAGGCAGCTCCTGCTTCACCAC |
| 63 | TPP1 | GGTGGCTTCAGCAATGTGTTCC | 64 | GAAGTAACTGGATGGTGGCAGG |

TABLE 1-continued

Primer sequences used in real-time PCR analysis.

| SEQ ID No. | Gene name | Forward primer | SEQ ID No. | Reverse primer |
|---|---|---|---|---|
| 65 | TMEM55B | CAGAGTTCACAGACCGCACTTTG | 66 | GGCAGTGACTGCCAAAAGCAAG |
| 67 | GAPDH | GTCTCCTCTGACTTCAACAGCG | 68 | ACCACCCTGTTGCTGTAGCCAA |
| Rat primers | | | | |
| 69 | Map1lc3a | AACAGGAGAAGGATGAAGACGG | 70 | TTGACTCAGAAGCCGAAGGTTT |
| 71 | Lamp1 | GCACCTCCAACTATTCCCTGAA | 72 | ACAGACCCAAACCTGTCACTTT |
| 73 | Tfeb | AATGGGAGCAACCGTACTTAGG | 74 | GAGGGAAGACAGGTCCATGAAG |
| 75 | Atp6v1h | CTCAGTATGTGCAGTGTGTTGC | 76 | TACAGTTCACCCCATCTGCTTC |
| 77 | Vps18 | GCTGATGATTCGCTCCATTGAC | 78 | AGTCTGGTAGCTGTATCCCTGT |
| 79 | Actb | CTGTGTGGATTGGTGGCTCTAT | 80 | GTAACAGTCCGCCTAGAAGCAT |

Western Blotting and Immunoprecipitation.

Cells are lysed on ice in 1× Lysis Buffer (9803, Life Technologies) with complete protease inhibitor mixture (04693124001, Roche Applied Science). Animal tissues are homogenized in nine volumes of ice-cold PBS supplemented with protease inhibitors. Cytosolic and nuclear fractions are isolated using protocols similar to those described previously. Anti-Flag or TFEB antibody is added to the whole cell lysates and Dynabeads® Protein G (10003D, Life Technologies) is used for immunoprecipitation. Proteins are separated by 10-15% SDS-PAGE, transferred, and blotted with the antibodies described. The blots are then incubated with secondary antibodies or the Clean-Blot IP Detection Reagent (21230, Thermo Scientific) at room temperature for 1 h. The protein signals are detected by ECL kit (32106, Pierce) and quantified using ImageJ software.

Immunocytochemistry.

Cells are seeded on coverslips placed in 24-well plates. After drug treatment, slices are fixed with 3.7% paraformaldehyde, permeabilized in 0.2% Triton X-100 and blocked with 5% BSA. After blocking, the slices are stained with anti-TFEB (1:200) or anti-Flag (1:500) antibodies overnight at 4° C. Alexa Fluor®488 (green) or Alexa Fluor®594 (red) secondary antibodies (1:500) are added for 1 h at room temperature. After nuclear staining with DAPI, the slices are mounted with FluorSave reagent (345789, Calbiochem). Cells are visualized using an Eclipse 80i fluorescence microscope (Nikon Instruments Inc.)

Statistical Analysis.

Each experiment is performed at least 3 times, and the results are presented as mean±SD. One-way analysis of variance (ANOVA) followed by the Student-Newman-Keuls test using the SigmaPlot 11.0 software packages. A probability value of $P<0.05$ is considered to be statistically significant.

Translation of Animal Dosage to Human Dosage.

The effective dosage of the invented curcumin mono-carbonyl analog C1 in mice ranges from 5 mg/kg (body weight) to less than 20 mg/kg (body weight) per day. According to the dose translation formula (Reagan-Shaw Si, et. al., *Dose translation from animal to human studies revisited. FASEB J.* 2008; 22(3):659-61.), the effective translated adult human dose of the curcumin mono-carbonyl analog C1 of the present invention ranges from 0.41 mg/kg (body weight) to less than 1.62 mg/kg (body weight) per day.

Preferred Embodiments of the Present Invention

Pharmacokinetic Study of Curcumin Analog C1 and Curcumin

Animals and Treatment

Materials and Methods

Male C57BL/6 mice and Sprague Dawley rats were purchased from Chinese University of Hong Kong, acclimatized in Hong Kong Baptist university animal house for 2 weeks. Animals were kept for 18 h fasting before the experiment. Curcumin analog C1 and curcumin were suspended in 1% CMC-Na at 10 mg/kg, given to animals through oral route at 10 ml/kg dosing volume. Blood (by heart puncture) and brain samples were collected starting from 0.25, 0.5, 1, 2, 4, 6, 8, 12 and 24 h time points (n=3 for each time point) under chloral hydrate anesthesia at 500 mg/kg (I.P. injection). Based on mice pharmacokinetic study, rat blood, brain and cerebrospinal fluids (CSF) were collected at 30 minutes time point (n=4). All blood samples were collected in heparinized tubes. Plasma was collected by centrifuging at 10,000 rpm for 10 minutes at 4° C. Blood, brain and CSF were stored in −80° C. until further analysis.

Cerebrospinal Fluid Collection

Cerebrospinal fluid (CSF) was collected by puncturing Cisterna Magna. Briefly, stereotaxic apparatus (Stoelting, Wood Dale, USA) was used for CSF collection. The tip of CSF collection needle (21G) was placed at the center of stereotaxic apparatus ear bars contact and considered it as zero point. Then rats were anaesthetized with chloral hydrate at 500 mg/kg in saline through intra-peritoneal route. Rats were fixed on the stereotaxic apparatus with 3 cm elevated body position. Rat head was positioned at nearly 110° angle between stereotaxic apparatus frame and rat nose. Cisterna magna location was identified by a 3 mm² depressed area between the spine and occipital protuberance in mid-sagittal plane, at 10-12 mm approximate distance from ear. The collection needle was inserted into the Cisterna magna from zero point at A-P: −1.5±1 mm, M-L: 0 mm and D-V: not more than 4-6 mm (from the skin surface). The needle was connected to a 1 ml syringe through a silicon tube. By applying a gentle negative pressure through 1 ml syringe, 100 μl of CSF without any blood contamination was collected.

Brain Sample Preparation

Whole brain and brain parts were homogenized with 2 weight/volumes of PBS (pH=3.2), spiked with 10 μl of internal standard salbutamol (200 ng/ml in methanol). The homogenate was liquid-liquid extracted with 1 ml of ethyl acetate. 50 μl of 0.5M sodium hydroxide was added to the brain homogenate for efficient C1 extraction. After vigorous sonication and vortex mixing, samples were centrifuged at 15,000 RPM for 10 min. The supernatant was collected and vacuum dried. The samples were reconstituted with 100 μl of mobile phase (0.1% formic acid in acetonitrile), vortex mixed and transferred to an amber colored sampler vial with plastic insert.

Plasma and CSF Sample Preparation

100 μl of plasma and CSF was mixed with 100 μl of PBS (pH=3.2), 10 μl of 0.05 M sodium hydroxide and spiked with 10 μl of salbutamol (200 ng/ml in methanol). The mixture was liquid-liquid extracted with 500 μl of ethyl acetate. After vigorous sonication and vortex mixing, samples were centrifuged at 15,000 RPM for 10 min at 4° C. The supernatant was collected and vacuum dried. The samples were reconstituted with 100 μl of mobile phase (0.1% formic acid in acetonitrile), vortex mixed and transferred to an amber colored sampler vial with plastic insert.

LC/MS/MS Condition

UPLC 1290 (Agilent technologies, CA, USA) with binary pump, autosampler system, column with thermostat, vacuum degasser and 6460 QQQ Mass spectrometer was used for compound detection. Chromatographic separation was achieved by waters BEH-C18 (1.7 μm, 2.1×50 mm) column maintained at 40° C. Sample solutions (3 μl) were eluted with mobile phase consisting of 0.1% formic acid in water (A) and 0.1% formic acid in acetonitrile (B). Gradient elution was performed with the following solvent transition rate: 0-5 min, 30% solvent B; 5-5.1 min, 30-80% solvent B; 5.1-7 min, 80-100% solvent B; 7-7.1 min, decreased from 100-30% solvent B and finished with 30% solvent B from 7.1-9 min at 0.35 ml/min constant flow rate. Agilent 6460 Quadrupole MS with electron spray ionization (ESI) source with jet stream technology was used to produce positive MS/MS precursor ions with the following MS operational parameters: nitrogen as collision gas with capillary voltage 4 kV, 8 L/min sheath gas flow rate, sheath gas temperature at 350° C., nebulizing gas temperature 300° C., 45 psi nebulizer pressure and 90V fragment voltage. Collision energies are 11 eV for C1, curcumin and 12 eV for salbutamol. MRM ion mode was used to monitor 369.1>285.1 m/z for curcumin, 295.1>187.1 m/z for C1 and 248>148 m/z for salbutamol precursor-to-product ion transitions. Mass data were collected and processed using Agilent technologies Mass hunter B.03 software QQQ software for both qualitative and quantitative analysis.

Preparation of Stock Solutions and Calibration of Standards:

Stock solutions of C1 and curcumin were prepared separately in methanol at of 1 mg/mL concentration and stored in −80° C. Working solution of salbutamol was prepared by diluting the stock solution with mobile phase to 200 ng/ml. 8 calibration standards were prepared separately by spiking 100 μl of blank plasma and 100 μl of brain homogenate with 10 μl of the calibration standards containing IS in the to achieve final concentration in the range of 200-0.78 ng/ml.

Evaluation of the Anti-AD Efficacy of Curcumin Analog C1 in AD Animal Models

Animals and Treatment

Male 5×FAD mice were purchased from Jackson laboratories (Stock number 006554) and maintained at 23±2° C. temperature, 60±15% relative humidity with free access to food and water ad libitum. 5×FAD male mice were inbred with wild-type (WT, C57/BL6) female mice to produce heterozygous offspring. Offspring were genotyped to select 5×FAD (APP KM670/671NL (Swedish), APP I716V (Florida), APP V717I (London), PSEN1 M146L (A>C), PSEN1 L286V) gene mutations mice. Two months old WT and 5×FAD mice (male and female, n=10-14 per group) were treated daily with vehicle (1% sodium carbonyl methylcellulose [CMC-Na; Sigma-Aldrich, C5678]), curcumin analogue C1 (5 mg/kg, 10 mg/kg) or curcumin (50 mg/kg; Sigma-Aldrich, 08511) suspended in 1% CMC-Na by oral gavage for 4 months.

Homozygous 3×Tg mice (APP KM670/671NL (Swedish), MAPT P301L, PSEN1 M146V) were produced in Hong Kong Baptist University animal house and maintained at 23±2° C. temperature, 60±15% relative humidity with free access to food and water ad libitum. Seven months old WT (129/SvJ, n=6 for male mice; n=10 for female mice) and 3×Tg mice (n=6 for male mice; n=10 for female mice) were treated daily with vehicle (1% CMC-Na; Sigma-Aldrich, C5678]), curcumin analogue C1 (2.5 mg/kg, 5 mg/kg, 10 mg/kg) or curcumin (50 mg/kg; Sigma-Aldrich, 08511) suspended in 1% CMC-Na by oral gavage for 7 months.

All animal care and experimental procedures were approved by the Hong Kong Baptist University Committee on the Use of Human and Animal Subjects in Teaching and Research.

Contextual Fear Conditioning

Contextual fear conditioning (CFC) was used to evaluate the fear memory reconsolidation of 5×FAD mice after treatment. The experiment was conducted 30 min after the drug treatment in ANY maze fear conditioning system under licensed ANY maze tracking system connected to a Windows XP computer. A digital camera was installed on each chamber and signals were sent to the computer for analysis. The experiments were conducted in two sound proof chambers. All the experiments were conducted with continuous 40 units of white noise and 40 lux white light. During training, mice were allowed to explore the platform for 2.5 min and then received 3 repeated footshock cycles (30 s) at 30 s intervals, each started with a cue tone (28 s, 1500 Hz) and ended by a footshock (30.0 mA, 2 s). On the second day the mice were allowed to explore the platform for 3 min followed by a cue tone (30 s, 1500 Hz) without footshock, and the freezing time was recorded. Contextual fear memory formation and the subsequent remote memory stabilization were evaluated by scoring freezing index (the absence of all but respiratory movement).

Open-Field Test

3×Tg mice were treated with the indicated compounds for 7 months and then the open-field test was performed to evaluate the exploratory behavior in novel environment. The experiment was conducted 30 min after last dosing time. Mice placed in the center of an empty open field (25 cm×25 cm) were allowed to explore the environment for 5 min without any external disturbance. Ethnovision XT software was used to measure the patterns of movement, time spent in the center and margin, velocity, distance traveled as indicators of agility and exploration.

Morris-Water Maze

3×Tg mice were treated with the indicated compounds for 7 months and Morris-water maze (MWM) was used to evaluate the spatial learning memory. MWM is a circular water (21±1° C.) container with 1 meter diameter. Animals were pre-quarantined and acclimatized to the experimenting room at least 1 week before the start of the experiment. The experiment was started with one day visual platform trial. Each mouse underwent 4 visible platform trails (each trial 60 seconds) with different platform placement, positioned above the water level. Hidden platform training was conducted after mixing a non-toxic paint in the water. Mice were trained for 6 continuous days, each day composed of different session with 4 hidden platform trials (each trial 60 seconds). Each session was designed with randomized animal introduction pattern into the water maze with unchanged platform position. Each trial was conducted with 30 min inter-trial interval and provided with external cues. To assess the long term spatial memory retrieval a probe trial (60 seconds) was conducted 24 h after the last training session. During probe trial water maze was divided into 4 quadrants. The hidden platform in the target quadrant was removed after determining its location. Ethnovision XT software was used to observe and record the swimming pattern. During hidden platform training sessions, time spent to find the platform was taken as a parameter to evaluate memory acquisition. In probe trial percentage of time spent in the target quadrant compared to the other 3 quadrants was calculated.

Tissue Extraction and Western Blotting Analysis

Brain tissues were lysed with RIPA buffer (TBS with 1% NP-40, 1% sodium deoxycholic acid, 0.1% SDS, and protease phosphatase inhibitor cocktails) and centrifuged at 15,000 RPM for 30 min. Supernatant is collected and the pellets were further lysed with 2% SDS in RIPA buffer. Protein concentration was estimated by BCA assay. Protein lysates were separated by 10-15% SDS-PAGE, transferred onto PVDF membrane, blocked with non-fat milk, incubated overnight with full-length APP (51-2700, Thermo Fisher), 6E10 (803017, Biolegend), PHF1 (kindly provided by Prof. Peter Davies at Albert Einstein College of Medicine), AT8 (MN1020, Thermo Fisher), total Tau (A0024, Dako), LC3B (Novus), TFEB (A303-673A, Bethyl Laboratories), and then the respective secondary antibodies for 2 h at room temperature. Protein chemiluminescence signal was detected by using ECL kit and quantified using ImageJ software.

Immunohistochemistry

Mice half brains were fixed with 4% paraformaldehyde in PBS overnight and dehydrated in 30% sucrose in PBS for at least 24 h. Brain sections (30 μm) were cut on a microtome and stored at 4° C. in PBS+0.1% sodium azide. Sections were permeabilized for 10 min with cold PBS containing 0.5% Triton X-100 and blocked with 3% bovine serum albumin for 1 h at room temperature. The sections were incubated with biotinylated 4G8 antibody (800701, Biolegend) overnight, and then incubated with Avidin-Biotin enzyme complex (Vecstatin-ELITE ABC-HRP kit) and Aβ plaques were visualized by DAB peroxidase and quantified using ImageJ software.

Statistical Analysis

All data are presented as Mean±SEM. One-way analysis of variance (ANOVA) followed by the Dunnett's Multiple Comparison Test, or Two-way ANOVA followed by Bonferroni post-hoc test was performed using the GraphPad Prism 5.03. A probability value of $P<0.05$, $P<0.01$, $P<0.001$ was considered to be statistically significant.

Results

Curcumin Analog C1 Shows Good Bioavailability In Vivo.

The neuroprotective effects of curcumin have been well-documented in literature; however, further clinical applications were limited by its poor bioavailability. Recently the inventors of the present invention identified a mono-carbonyl derivative of curcumin as an activator of the transcription factor EB (TFEB), which controls autophagy and lysosome biogenesis (US patents under U.S. Pat. Nos. 9,351,946 and 9,540,299, which are incorporated herein by reference in their entirety), thereby becoming a promising target for the treatment of neurodegenerative diseases including Alzheimer's disease (AD). Here the inventors of the present invention first compared the pharmacokinetic profiles of curcumin analog C1 and curcumin. The results show that C1 has much higher blood and brain bioavailability than curcumin in C57BL/6 mice. In the brain, C1 reached the maximum concentration ($C_{max}$) of 1308.23±88.96 ng/g at 30 min ($T_{max}$), while curcumin achieved $C_{max}$ of 73.77±0.24 ng/g at 60 min ($T_{max}$) when each compound was given orally at the dosage of 10 mg/kg [FIGS. 1(A) and (B)]. Based on the $C_{max}$ of C1, the inventors of the present invention further determined the concentration of C1 in different brain regions of SD rats 30 min after oral administration of C1 (10 mg/kg). In the frontal cortex and hippocampus the concentration of C1 was 57.97±18.65 ng/g and 68.41±21.72 ng/g respectively. In contrast, the concentration of C1 in the striatum is relatively lower (4.69±2.19 ng/g). Meanwhile, the level of C1 in plasma and CSF was determined to be 352.16±21.37 ng/ml and 101.5±52.41 ng/ml respectively [FIG. 1(C)]. These results indicate that C1 has much better systemic bioavailability than curcumin and therefore, predicting better efficacy in AD animal models.

Curcumin Analog C1 Reduces Aβ Plaques and Improves Memory Deficit in 5×FAD Mice

Figure 2:
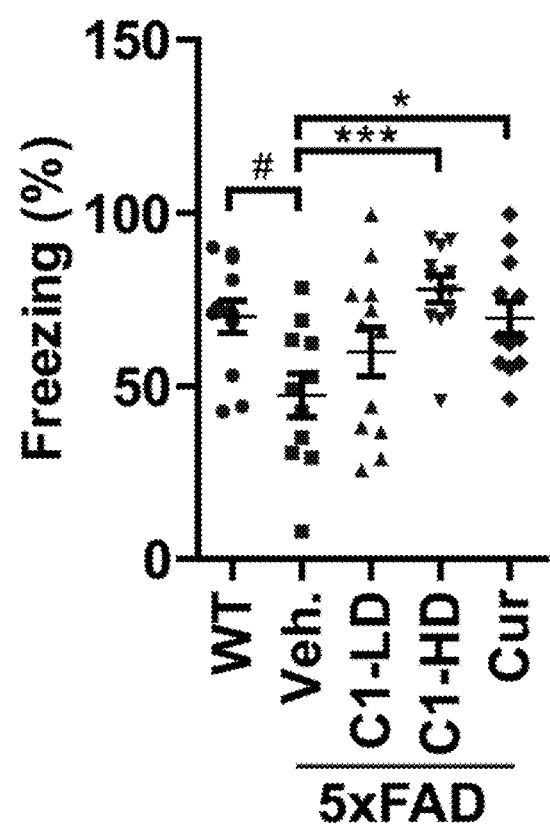
FIG. 2 shows curcumin analog C1 improves fear memory in 5×FAD mice. 5×FAD and wild type (WT) mice were orally treated with vehicle (Veh.), C1 (low dose, 5 mg/kg, LD; high dose, 10 mg/kg, HD) or curcumin (Cur, 50 mg/kg) for 4 months. The percentage of freezing in each group was quantified as mean±SEM (n=12 per group). #P<0.05 vs. WT; *P<0.05 vs. Cur; ***P<0.001 vs. C1-HD.
Figure 3:
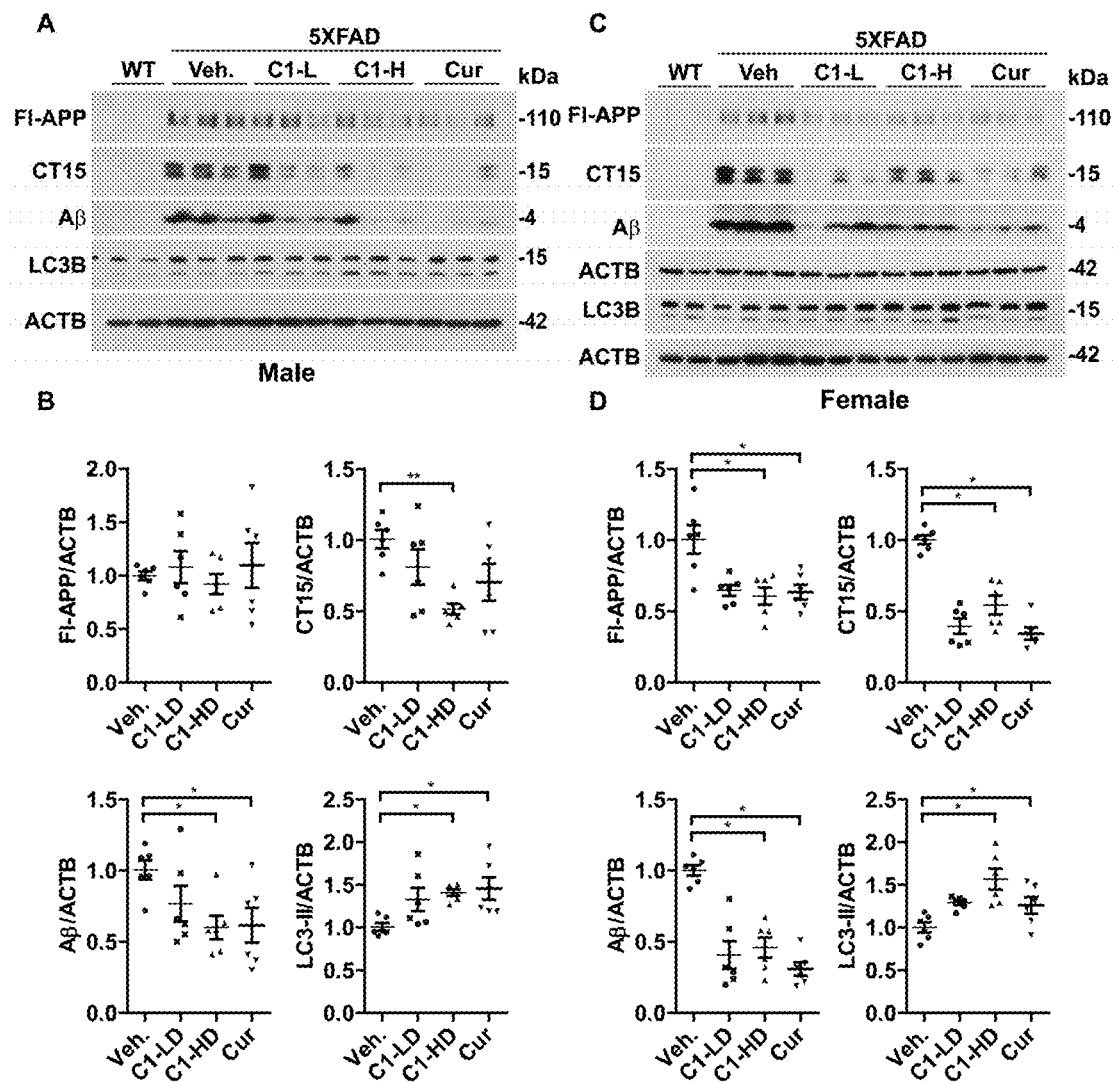
FIG. 3 shows effects of curcumin analog C1 on the degradation of amyloid precursor protein (APP), Aβ and autophagy. 5×FAD and wild type (WT) mice were orally treated with vehicle (Veh.), C1 (low dose, 5 mg/kg, LD; high dose, 10 mg/kg, HD) or curcumin (Cur, 50 mg/kg) for 4 months: (A, C) Representative blots show the levels of full-length APP, APP fragment CT15, Aβ and autophagy marker LC3 in the brains of male (A) and female (C) mice; (B, D) Data are quantified as mean±SEM in male (B, n=6) and female (D, n=6) mice. *P<0.05 vs. Veh. treatment; **P<0.01 vs. Veh. treatment.

The defect in memory formation and retrieval dynamics of 5×FAD mice can be evaluated by contextual fear conditioning (Neurobiol Dis. 2007; 26(1):134-45.). Compared with the C57BL/6 WT mice, the freezing time of 5×FAD significantly decreased (P<0.05) (FIG. 2), which is consistent with the finding of Ohno et, al. (Neurobiol Learn Mem. 2009; 92(3):455-9.). C1 (10 mg/kg) and curcumin (50 mg/kg) treated mice showed significant memory reconsolidation evidenced by the increased freezing index compared with the vehicle treatment (P<0.001 for C1 and P<0.05 for curcumin) (FIG. 2). Accordingly, C1 shows better memory improvement than curcumin in 5×FAD mice.

Figure 4:
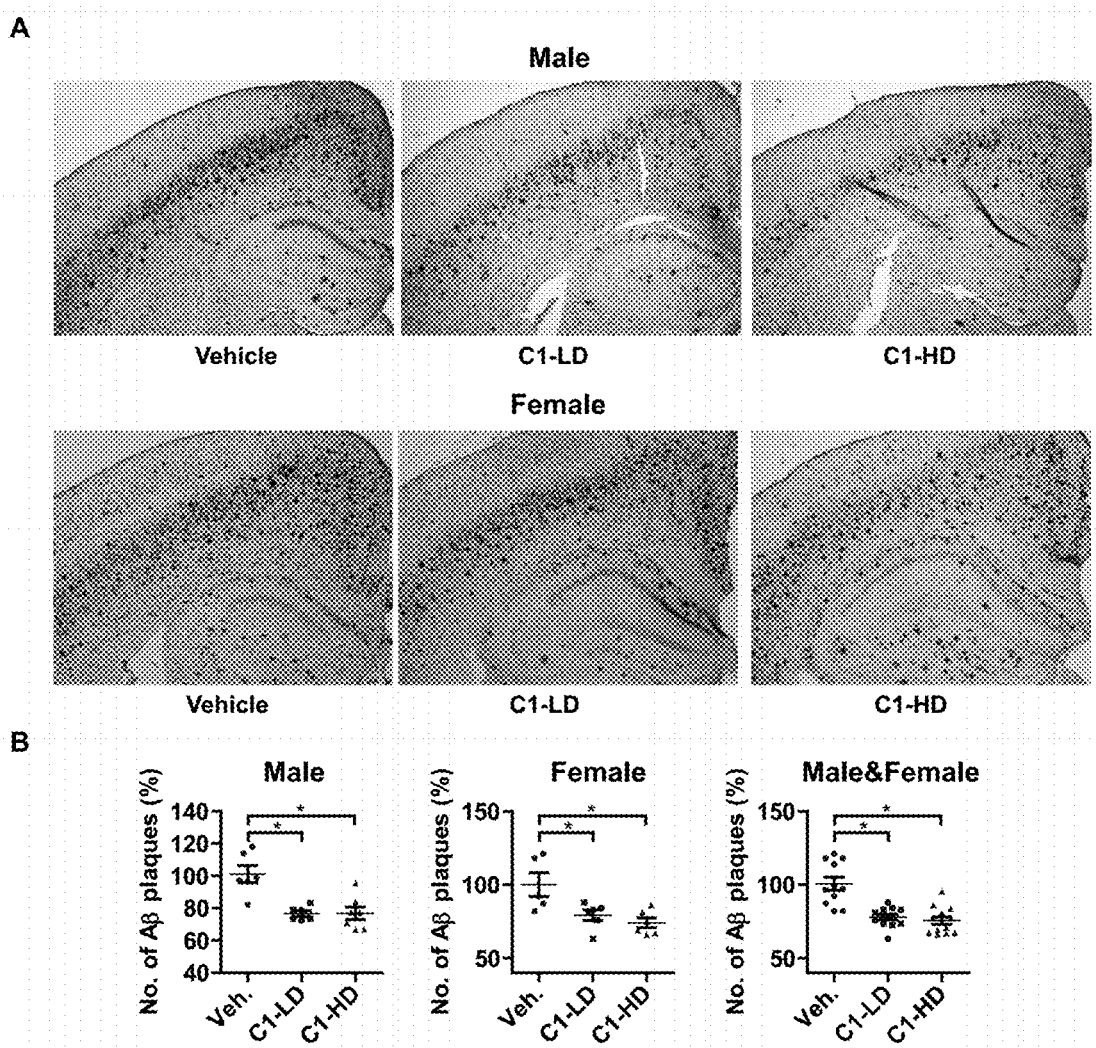
FIG. 4 shows effects of curcumin analog C1 on the degradation of cortico-hippocampal Aβ plaque load in 5×FAD mice brains: (A) Representative images show the Aβ plaques labeled with biotinylated 4G8 antibody; (B) Data are quantified as mean±SEM in male (n=6), female (n=6) and the combined (n=12). *P<0.05 vs. Veh. treatment.

After behavioral test, each brain was cut into half and used for immunoblots and immunohistochemistry analysis separately. The levels of APP and its metabolic products CTFs and Aβ were determined in each group. In both male and female mice, Both C1 (10 mg/kg) and curcumin (50 mg/kg) treatment significantly reduced the levels of APP CTFs and A3, accompanied with autophagy enhancement indicated by the increase in LC3-II levels [FIG. 3(A)-(D)]. Notably, C1 and curcumin treatment also reduced Fl-APP levels in female 5×FAD mice. Generally, the effects of C1 on APP and Aβ degradation are better in female than male mice. The effects of C1 on Aβ plaque load were further determined by immunostaining and the quantification results showed significant reduction of Aβ plaque load in cortico-hippocampal sections of mice treated with low dosage (5 mg/kg) and high dosage (10 mg/kg) of C1 [FIG. 4(A)B)]. These results indicate that C1 promotes the degradation of APP fragments and Aβ by enhancing autophagy in the brains of 5×FAD mice.

Curcumin Analog C1 Ameliorates Both APP and Tau Pathology and Improves Memory in 3×Tg Mice To further prove the anti-AD efficacy of curcumin analog C1, the inventors of the present invention selected the 3×Tg mouse expressing APP KM670/671NL (Swedish), MAPT P301L and PSEN1 M146V, which exhibits more severe cognitive defect. Six months old 3×Tg mice were treated with C1 or curcumin for 7 months. The open field test and Morris water maze were applied to evaluate the memory improvement and molecular changes in APP, Tau, TFEB and autophagy were determined.

Figure 5:
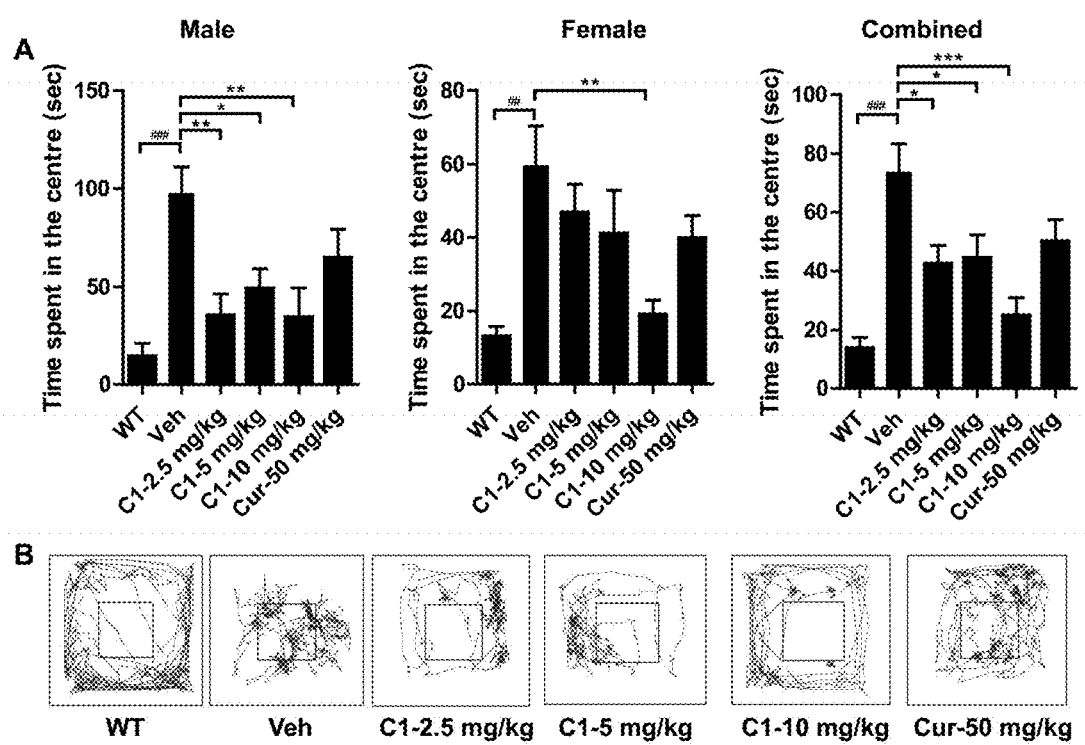
FIG. 5 shows Curcumin analog C1 improved the open field exploratory behavior in 3×Tg mice. 3×Tg and wild type (WT) mice were orally treated with vehicle (Veh), C1 (2.5 mg/kg, 5 mg/kg, 10 mg/kg) or curcumin (Cur, 50 mg/kg) for 7 months: (A) Quantification of time spent in the center for each treatment (mean±SEM) in male (n=6), female (n=10) and the combined (n=16). ##P<0.01, ###P<0.001 vs. WT; *P<0.05, P<0.01, *P<0.001 vs. Veh. Treatment; (B) Representative exploratory patterns of mice in each group are shown.
Figure 6:
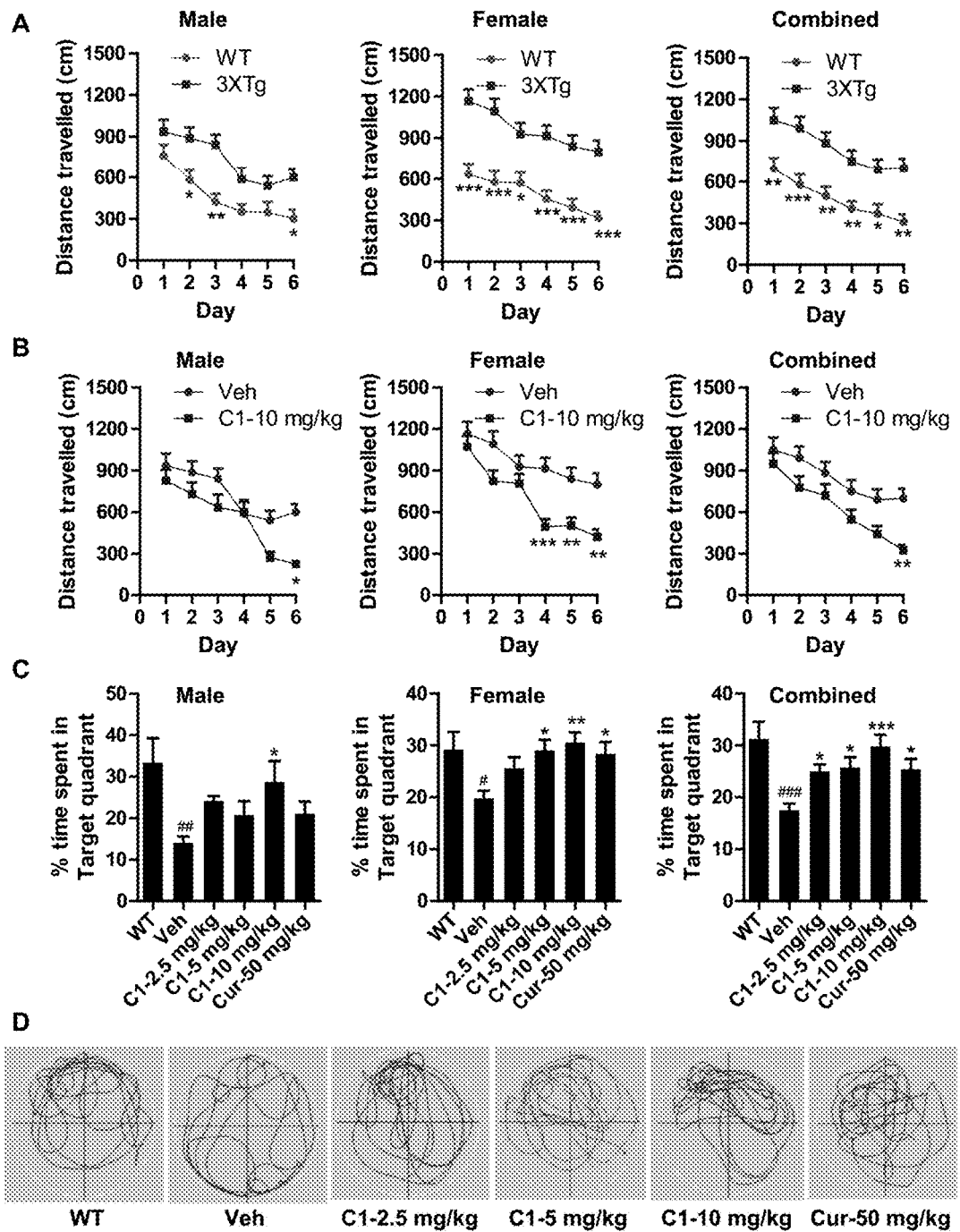
FIG. 6 shows curcumin analog C1 improved spatial learning and memory acquisition in 3×Tg mice determine by Morris-water maze. 3×Tg and wild type (WT) mice were orally treated with vehicle (Veh), C1 (2.5 mg/kg, 5 mg/kg, 10 mg/kg) or curcumin (Cur, 50 mg/kg) for 7 months: (A) Quantification of the distance traveled (mean±SEM) to find the hidden platform for WT and 3×Tg mice (male, n=6; female, n=10; and the combined, n=16); (B) Quantification of the distance traveled (mean±SEM) to find the hidden platform for 3×Tg mice treated with vehicle (Veh) or C1 (10 mg/kg) (male, n=6; female, n=10; and the combined, n=16). *P<0.05, P<0.01, *P<0.001 vs. Veh. Treatment; (C) Quantification of time spent in the target quadrant (mean±SEM) for each treatment group (male, n=6; female, n=10; and the combined, n=16) in the probe trials. #P<0.05, ##P<0.01, ###P<0.001 vs. WT; *P<0.05, P<0.01, *P<0.001 vs. Veh. Treatment; (D) Representative moving patterns of mice in each group in the probe trials are shown.

In the open field test, the 3×Tg mice stayed much longer time in the center compared with the WT mice (P<0.001) [FIG. 5(A)B)]. In contrast, C1 treatment dose-dependently decreased the time spent in the center compared with vehicle treatment. The 3×Tg mice treated with the high dose of C1 (10 mg/kg) almost recovered the exploratory behavior to the levels of WT mice (P<0.001) [FIG. 5(A)B)]. However, curcumin treatment showed no significant improvement of 3×Tg mice in the open field test. In Morris water maze test, the 3×Tg mice (both male and female) traveled longer distance than the WT mice to find the hidden platform during the training days [FIG. 6(A)D)]. In contrast, the mice treated with C1 (10 mg/kg) significantly reduced the distance traveled to find the hidden platform [FIG. 6(B)] compared with vehicle treatment. In probe trial, the 3×Tg mice treated with C1 (2.5, 5, 10 mg/kg) or curcumin (50 mg/kg) significantly increased the percentage of time spent in the target quadrant when compared to the vehicle treatment [FIG. 6(C)-(D)]. Notably, 3×Tg mice treated with C1 (10 mg/kg) showed much better improvement in target recognition than curcumin (50 mg/kg) treatment. These results indicate C1 ameliorates spatial learning and memory impairment in 3×Tg AD mice.

Figure 7:
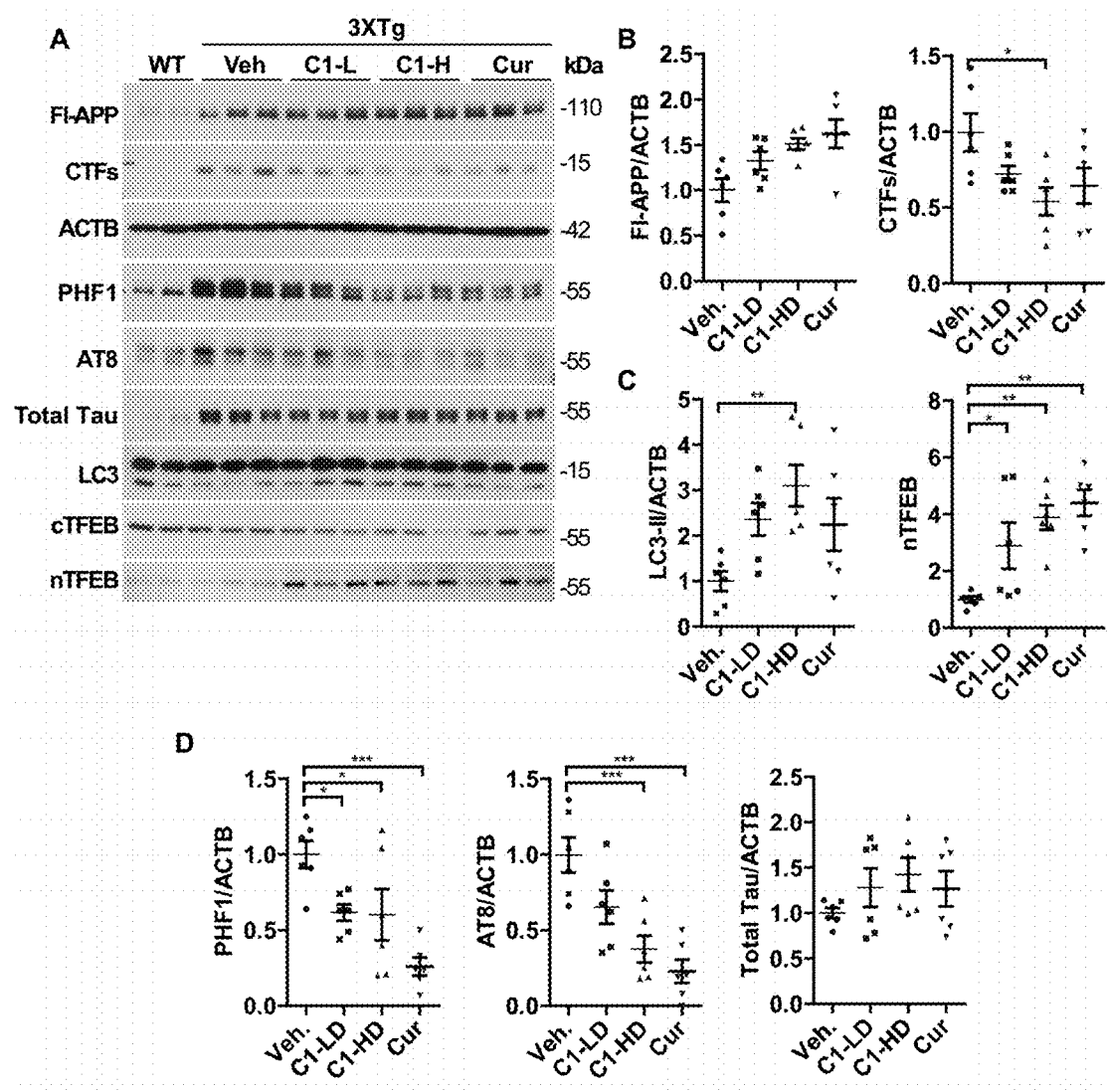
FIG. 7 shows curcumin analog C1 attenuates both APP and Tau pathology and enhances autophagy in 3×Tg mice. 3×Tg and wild type (WT) mice were orally treated with vehicle (Veh), C1 (2.5 mg/kg, 5 mg/kg, 10 mg/kg) or curcumin (Cur, 50 mg/kg) for 7 months: (A) Representative blots show the levels of full-length APP (Fl-APP), APP carboxy terminal fragments (CTFs), phosphorylated Tau (PHF-1, AT-8), total Tau, cytosolic and nuclear TFEB (cT-FEB, nTFEB) and LC3 in the brains of female mice treated with indicated compounds; (B-D) Data are quantified as mean±SEM (n=6) for (B) Fl-APP and CTFs, (C) LC3-II and nTFEB, and (D) PHF-1, AT-8 and total Tau. *P<0.05, P<0.01, *P<0.001 vs. Veh. treatment.
Figure 8:
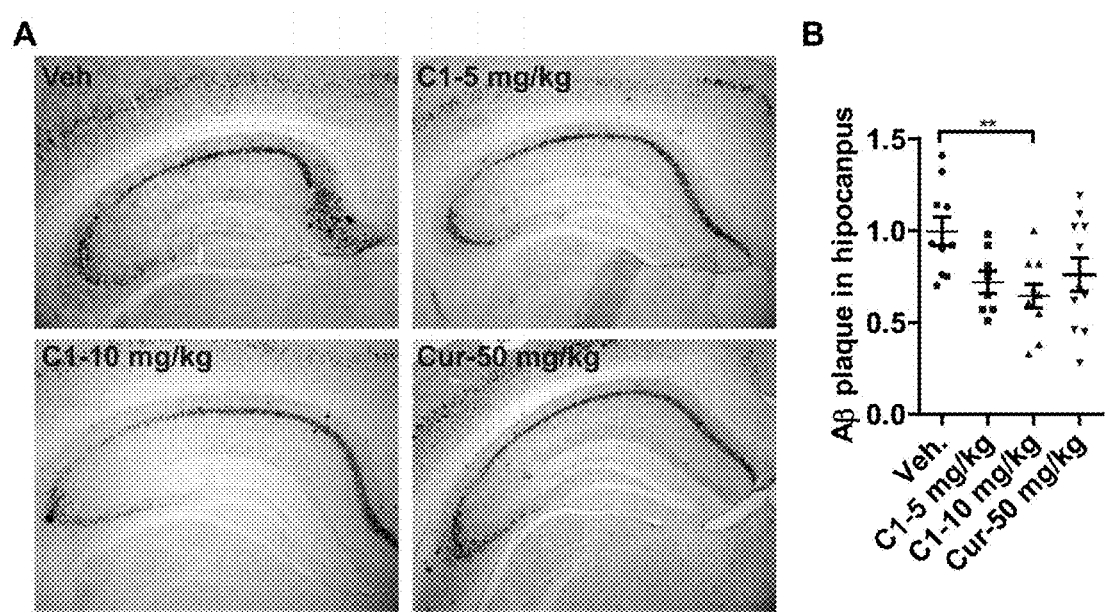
FIG. 8 shows Curcumin analog C1 reduces hippocampal Aβ plaque load in 3×Tg mice brain. After treatment, 3×Tg mice brain coronal sections were labeled with biotinylated 4G8 antibody and quantified: (A) Representative images show the Aβ plaques labeled with biotinylated 4G8 antibody; (B) Data are quantified as mean±SEM (n=8-11). *P<0.01 vs. Veh. treatment.

To determine whether the effects of C1 on memory improvement in 3×Tg mice is contributed by its ability to attenuate APP and Tau pathology, the levels of different forms of APP and Tau in the hippocampus of female mice were semi-quantified by immunoblots. As shown in FIG. 7, the overexpression of APP and Tau in 3×Tg mice was verified when comparing with the WT mice. For APP and Aβ, C1 high dose (10 mg/kg) significantly reduced hippocampal CTFs, but not Fl-APP levels [FIG. 7(A)-(B)], and reduces hippocampal Aβ plaque load [FIG. 8(A)-(B)]. However, curcumin (50 mg/kg) treatment showed no significant reduction on CTFs and Aβ load. For Tau species, both C1 (10 mg/kg) and curcumin (50 mg/kg) treatment significantly decreased the levels of phosphorylated Tau (PHF1, AT8), but not the total Tau [FIGS. 7(A) and (D)]. These results indicate that C1 efficiently promotes the degradation of APP fragments, Aβ and phosphorylated Tau aggregates. Furthermore, the results showing that C1 significantly increased the levels of nuclear TFEB and LC3-II [FIGS. 7(A) and (C)] support the hypothesis that C1 promotes the autophagic degradation of protein aggregates in AD by activating TFEB.

The TFEB Activator C1 Restores Lone-Term Dotentiation (LTP) in 5×FAD Mice

Materials and Methods:

Heterozygous male 5×FAD mice purchased from Jackson laboratory (#006554) were maintained HKBU animal house at 23±2 OC and 60-15% relative humidity with free access to feed and water ad libitum. Male 5×FAD mice were bred with female wild-type C57BL/6. The produced heterozygous litters were maintained until their age 2 months. At 2 months age tail sample is collected in Non-ionic detergent buffer (50 mM KCL, 10 mM Tris-HCL, 2.5 mM mgCl2, 0.1 mg/ml Gelatin, 0.45% v/v NP-40, 0.45% v/v Tween 20 and 100 μgm/ml Proteinase K). Tail samples were incubated in 55° C. for overnight and denatured at 95° C. for 5 mins. Denatured samples were centrifuged, and supernatant is used for genotyping. Mice tail samples were genotyped using standard PCR protocol by using GoTaq G2 Green Master Mix (M7822), for APP, Forward 5'-AGGACTGAC-CACTCGACCAG-3' (SEQ ID NO: 81) and reverse, 5'-CGGGGGTCTAGTTCTGCAT-3' (SEQ ID NO: 82). After polymerase chain reaction amplification mice overexpressing APP transgene at 377 bp were isolated and maintained.

Mice Treatment:

Three-month old female c57BL/6 mice and heterozygous female 5×FAD mice were treated with vehicle (1% carboxy methyl cellulose) or 10 mg/kg of C1 through oral route for 3 months (n=6 for each group).

Electrophysiology:

Brain slice preparation: Wild type and 5× mice treated with or without C1 were cervical dislocated and rapidly brain was removed and placed in oxygenated ice-cold sucrose buffer (213 mM sucrose, 10 mM D-glucose, 2.5 mM KCL, 1.25 mM $KH_2PO_4$, 2.5 mM $CaCl_2$, 10 mM $MgSO4.7H_2O$, 75 mM NaCl and 650 mM $NaHCO_3$). 350 μm horizontal brain slices were cut using vibratome (Campden-5100). Brain slices were transferred and incubated in oxygenated Artificial Cerebro-Spinal Fluid (ACSF- 10 mM D-glucose, 3.5 mM KCL, 1.25 mM $KH_2PO_4$, 2.5 mM $CaCl_2$, 1.5 mM $MgSO4.7H_2O$, 75 mM NaCl and 650 mM $NaHCO_3$) at 30° C. for 1 hour. Slices were transferred into the MED64 2×8 multi-electrode array chamber. MEA stimulation electrodes were placed in close proximity to the hippocampal Schaffer-Collateral/Commissural pathway as well as recording electrode within CA1 region of hippocampus. ACSF was perfused at 2 ml/min. Field pulses with appropriate bi-phasic stimuli (10-60 μA for 0.2 millisecond with 20 seconds interval) delivered to Schaffer-Collateral/Commissural pathway. Suitable stimulus intensities were identified for each brain slice using I/O curve. Current amplitude with 40% of maximal amplitude is typically selected for each slice. After recording the baseline for 20 mins, Long term potentiation was induced by Theta burst stimulation (TBS). Slope of each Excitatory Post Synaptic Potential frequency (fEPSP) is calculated by using MED64-Quad II system and Mobius MED 64 software.

Figure 9A:
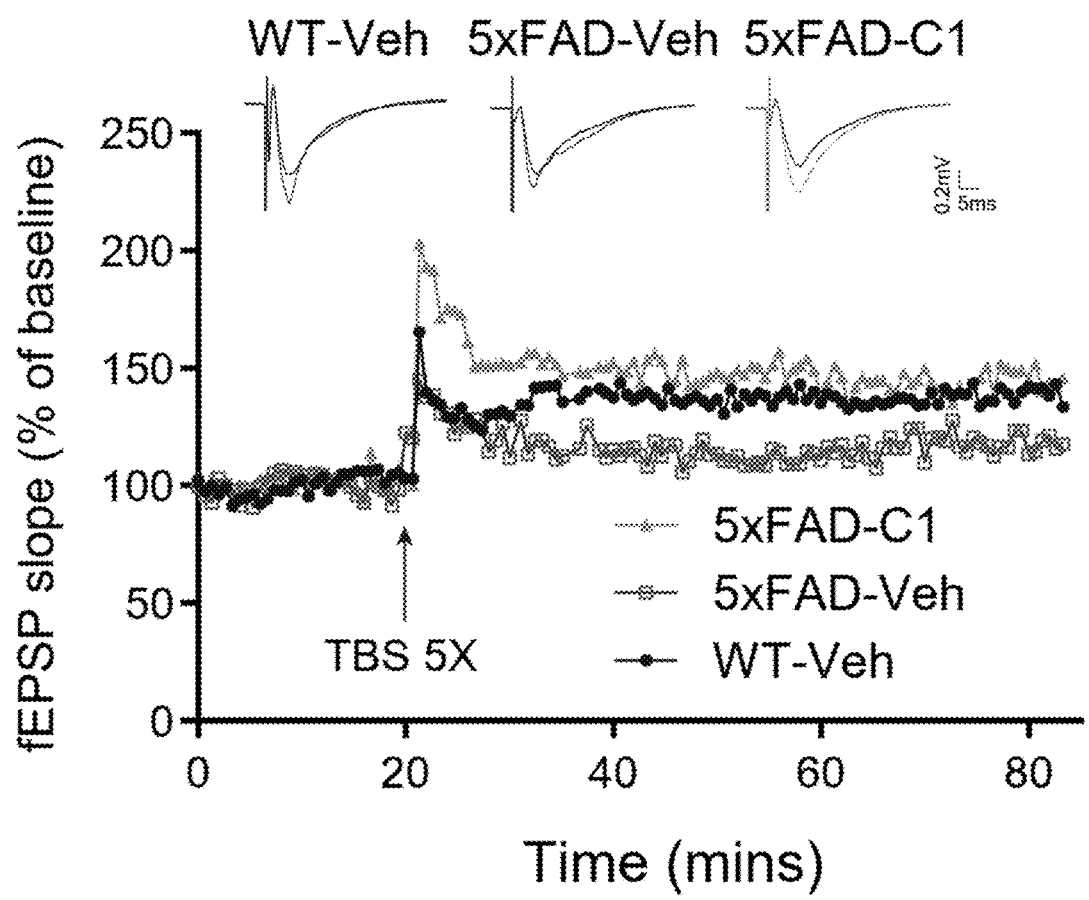
FIG. 9A and FIG. 9B show C1 restores synaptic plasticity in 5×FAD mice.
Figure 9B:
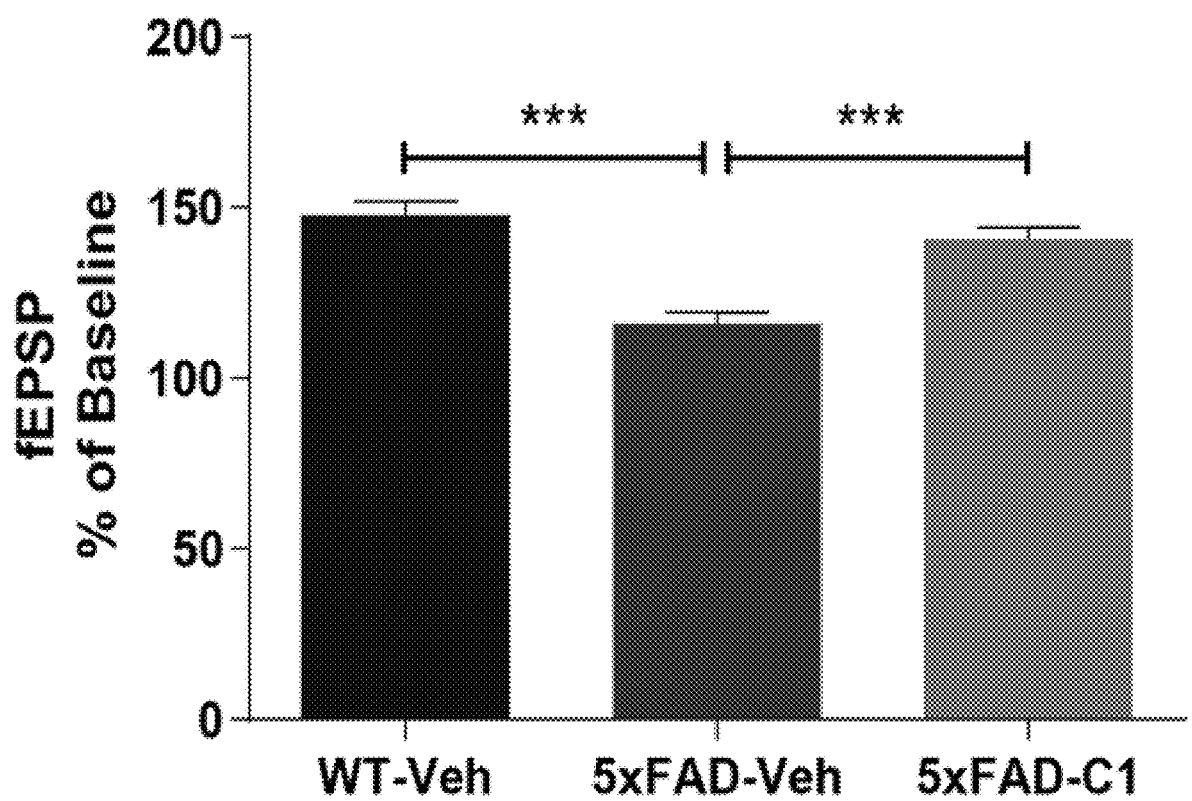

Results:

The usual cause of learning and memory impairment in Alzheimer's disease is due synaptic plasticity impairment. To further corroborate C1 ameliorating memory restoration in AD mice models, we further investigated synaptic plasticity restoration in 5×FAD mice. In the present invention, long-term potentiation induced by TBS was significantly impaired in 5×FAD mice compared to the similar age wild type mice (P<0.001). In C1 treated 5×FAD mice synaptic plasticity is significantly restored in comparison with vehicle treated 5×FAD control group (P<0.001) (FIGS. 9A and 9B). Together, these results indicate that C1 treatment can reverse synaptic dysfunction and ameliorate memory deficits in 5×FAD AD mice model.

The diseases that benefit from reverse synaptic dysfunction are diseases of neurodegenerative diseases such as Parkinson's disease, Alzheimer's disease, Huntington's disease, Frontotemporal dementia with parkinsonism-17 (FTDP-17), Pick disease (PiD), Progressive supranuclear palsy (PSP), Corticobasal degeneration (CBD) and Cerebral amyloid angiopathy.

INDUSTRIAL APPLICABILITY

The present invention discloses a method of use of a composition comprising an autophagy enhancement compound for treating neurodegenerative diseases. In particular, the said composition is used to treat the neural condition of synaptic dysfunction. Such neurodegenerative diseases are Parkinson's disease, Alzheimer's disease, Huntington's disease, Frontotemporal dementia with parkinsonism-17 (FTDP-17), Pick disease (PiD), Progressive supranuclear palsy (PSP), Corticobasal degeneration (CBD) and Cerebral amyloid angiopathy.

If desired, the different functions discussed herein may be performed in a different order and/or concurrently with each other. Furthermore, if desired, one or more of the above-described functions may be optional or may be combined.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

What we claim:

1. A method for reversing synaptic dysfunction and/or ameliorating memory deficits in a subject comprising administering a composition comprising an effective amount of a compound of formula C1:

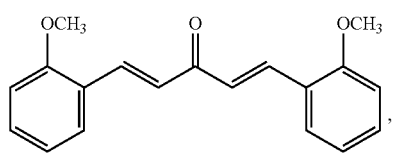

to said subject,
wherein said effective amount of said compound of formula C1 is from 0.41 to 0.81 mg/kg per body weight of said subject daily;
wherein levels of beta-amyloid plaque load, carboxy terminal fragments of amyloid precursor protein and phosphorylated Tau in cortico-hippocampal section of the brain of said subject are reduced after said administering;
wherein said subject is a human adult.

2. The method according to claim 1, wherein said synaptic dysfunction and/or memory deficits is/are conditions of or associated with neurodegenerative diseases comprising Parkinson's disease, Alzheimer's disease, Huntington's disease, Frontotemporal dementia with parkinsonism-17, Pick disease, Progressive supranuclear palsy, Corticobasal degeneration and Cerebral amyloid angiopathy.

3. The method according to claim 1, wherein the composition is administered orally to said subject in need thereof daily for at least three consecutive months.

* * * * *